United States Patent [19]
Kearney

[11] Patent Number: 5,424,209
[45] Date of Patent: Jun. 13, 1995

[54] AUTOMATED CELL CULTURE AND TESTING SYSTEM

[76] Inventor: George P. Kearney, 19237 Gunnerfield La., Germantown, Md. 20874

[21] Appl. No.: 34,542

[22] Filed: Mar. 19, 1993

[51] Int. Cl.$^6$ ............................................. C12M 3/00
[52] U.S. Cl. ................................. 435/284; 435/289; 435/290; 435/316; 435/809
[58] Field of Search .......................... 435/3, 284–286, 435/289, 290, 316, 809; 422/100; 222/103, 214

[56] References Cited

U.S. PATENT DOCUMENTS

| | | | |
|---|---|---|---|
| 3,836,335 | 9/1974 | Eppes | 422/100 |
| 3,895,741 | 7/1975 | Nugent | 222/103 |
| 3,941,662 | 3/1976 | Munder et al. | 435/284 |
| 4,629,686 | 12/1986 | Gruenberg | 435/284 |
| 4,650,766 | 3/1987 | Harm et al. | 435/284 |
| 4,999,298 | 3/1991 | Wolfe et al. | 435/3 |

FOREIGN PATENT DOCUMENTS

| | | | |
|---|---|---|---|
| 0224734 | 6/1987 | European Pat. Off. | 435/284 |
| 3525860 | 1/1987 | Germany | 435/316 |
| 0263789 | 1/1989 | Germany | 435/284 |

*Primary Examiner*—William H. Beisner
*Attorney, Agent, or Firm*—H. Jay Spiegel

[57] ABSTRACT

A cell culture and testing system provides a completely self-contained environment in which living tissues may be placed and where living tissues may be nutrified, oxygenated and maintained within a range of temperatures within which life may be sustained. The system includes aspects permitting administering of drugs or other substances to living tissues and monitoring of results accruing from such administration. In the preferred embodiment, the system is completely self-contained and sealed and may be operated both through use of an external power supply and an internal back-up power supply. The system is maintained at a positive pressure slightly above atmospheric pressure to prevent contamination from the surrounding environment. The system includes at least three levels of containment to completely isolate living tissues from ambient surroundings and the system has been successfully tested under conditions of zero gravity.

16 Claims, 18 Drawing Sheets

AUTOMATED CELL CULTURE AND TESTING SYSTEM

BACKGROUND OF THE INVENTION

Laboratory-scale culture and testing of cells and tissues derived from mammalian sources typically involves the use of specialized containers. The physical and chemical nature of the chosen vessel dictates the choice of handling methods and technical limitations of the experimental process. Static vessels such as petri dishes and tissue flasks, roller bottles which are rotated to provide continuous bathing of cells which grow attached to the walls of the vessel, or spinner flasks in which a moving paddle continually suspends cellular material in nutrient broth or media are commonly employed. In all of these approaches, the chosen vessel must be associated with a laminar flow hood for aseptic set-up and servicing. Furthermore, these vessels do not have independent means for controlling temperature. As such, such vessels must be placed within an incubator designed to regulate temperature and control atmosphere during maintenance.

In a further limitation, such vessels are, by design, open systems having direct gaseous communication with the ambient environment. For this reason, accidental contamination of the contents of the vessel with atmospherically borne microbial elements is common. When contamination with such ambient elements occurs, the user must reject the contents of the container from the particular study at hand, thereby causing loss of data and time. Systems which employ vessels, such as those listed above, are highly labor intensive, inconvenient, expensive, unreliable for maintenance of sterility and may also be wasteful of laboratory space.

While the prior art does evidence the existence of devices which, in limited ways, may be employed to grow and maintain living cells and tissues, most of these devices are incorporated into bioreactor-type inventions which utilize cells as living chemical fabricators to produce proteins, enzymes, monoclonal antibodies, hormones, drugs, pesticides and other substances. In such devices, the focus is on the desired end product and not on the cells themselves. The cells are simply the means to the end product meant for applications outside the system.

Given the limitations of known systems concerning sterility, contamination, reproducibility of results, size, expense and reliability, a need has developed for a single self-contained device able to sustain life of living cells and tissues, grow the tissues, facilitate performance of experimentation on the tissues and obtain results of such experimentation, free of risk of contamination, loss of sterility, and in a reproducible manner. It is with these thoughts in mind that the present invention was developed.

U.S. Pat. No. 4,725,548 to Karrer discloses a method and fermenter for growing tissue cells. In the Karrer device, once the cells are grown, they are transferred from the device via a harvest pipe for use external to the Karrer device. The present invention differs from the teachings of Karrer as contemplating a completely self-contained device wherein cells and other living tissues may be grown and wherein testing and experimental procedures utilizing these living tissues and cells occur within the confines of the completely self-contained device.

Several devices and systems are known in which cells and tissues are grown in gas permeable plastic bags. Those patents known to Applicant which employ such structure are U.S. Pat. Nos. 3,102,082 to Brewer, 3,941,662 to Munder et al., 4,142,940 to Modolell et al., and 4,829,002 to Pattillo et al. In such devices, the containers may be filled aseptically with media and bulk additives. System implementation is hampered by inherently limited cellular capacity and tedious turnover of media following application of hormones or drugs to the cultures. Systems such as those disclosed in these patents require use of an incubator to provide thermal and atmospheric maintenance. Passaging of cultured cells at confluence is done manually and the cells must be removed physically from the system. This transfer technique may facilitate contamination of cultured cells by microorganisms. Furthermore, the systems disclosed in these patents do not permit monitoring of the metabolic status of cells during culture. The present invention overcomes these deficiencies in these prior art designs.

An alternative to the static bag culture system is the hollow fiber bioreactor approach described in the Knazek et al. patents, U.S. Pat. Nos. 3,821,087, 3,883,393, 4,184,922, 4,200,689, 4,206,015 and 4,220,725. These systems employ membrane capillaries encased in rigid plastic housings sealed in such a manner that two discrete volumes are established which communicate via pores of molecular dimensions which traverse the membranes. The cells are inoculated into a static volume external to the capillaries. A mobile volume is contained within the membrane proper and the connected vessels and conduits. This volume may include a replenishable media reservoir and gas permeable tubing or membrane oxygenating devices which serve to adjust acidity in the media by allowing equilibration with controlled concentrations of carbon dioxide and facilitating uptake of oxygen. The media are circulated by means of a pump. While very high cell density is obtainable with the systems disclosed in these patents, direct observation of cells within the system is not feasible. In a further aspect, set-up must be accomplished under a laminar flow hood for aseptic set-up and servicing. Additionally, the systems disclosed in these patents must reside within a carbon dioxide incubator or equivalent cabinet. Furthermore, application of hormones or drugs is difficult and passaging of cells is manual, leading to potential for biological contamination.

U.S. Pat. No. 4,650,766 to Harm et al. discloses a culturing apparatus which is compatible with hollow fiber bioreactors such as those disclosed in the Knazek et al. patents. Patentees Harm and Peluso describe a culture apparatus which provides integral gassing of media and provision of heating to eliminate the need for incubators. The patented apparatus is limited by the fact that the system is of a single pass design resulting in inefficient use of media. Fluid flow is very slow resulting in loss of water through the exchange membrane. The osmolarity of the media increases to the detriment of the cells or tissues under culture. Dissolved gas components are the limiting nutrients in the system and new media is constantly moved over the cells to provide these materials. Open lines run from the outlet of the bioreactors to a supplemental fraction collector. The termination of these lines is open to the environment providing ready access for microbial contamination of the system. Gassing and heating of the medium is concurrent favoring formation of gas bubbles in the flow path. As is well known, presence of bubbles in a flowing system is lethal to cells in culture. Multiple media sources are mixed and distributed via manifolds thereby providing the potential for a single contamination nidus to infect all bioreactors in the system. While parallel flow paths are possible in the design, to thereby provide potential for reduction in the impact of casual contamination, gassing is continuous resulting in waste of supplies. Thermal regulation is determined by external water bath controls allowing the potential for rapid temperature variations which may be lethal. The Harm et al. system provides no automated control or monitoring nor is any facility for the introduction of drugs or hormones provided. Additionally, no computer control is provided.

U.S. Pat. No. 4,629,686 to Gruenberg discloses an apparatus for delivering a controlled dosage of a chemical substance to cell or tissue cultures. In the Gruenberg system, a series of pre-diluted media preparations are selectively applied to the organ or tissue of interest. A computer controls the selection of which concentration to apply. The system is single pass in design but does include a sterile dispenser for elimination of potential contamination via the fraction collector/emitter. Temperature is maintained via a circulating water bath providing potential for rapid temperature fluctuations which may be lethal to the tissues contained therein. The Gruenberg device may not be utilized for large scale testing of multiple drugs. The present invention differs from the teachings of Gruenberg as providing a multiple pass system, at least two levels of containment, provision for testing of multiple samples with multiple drugs simultaneously and as including extremely close control over nutrient supply, oxygenation and temperature.

U.S. Pat. No. 4,116,778 to Belousov et al. discloses a plant for continuous cultivation of microorganisms. Belousov et al. fail to contemplate administration of drugs or other substances to living tissues nor monitoring of results of such administration. Furthermore, Belousov et al. provide no control of the temperature of the cells therein. Other significant differences from the present invention also exist.

U.S. Pat. No. 4,894,342 to Guinn et al. discloses a bioreactor based fermenting device designed to grow cell products. Guinn et al. include a humidification process for gas, bubble arrestors and optical fluid level monitoring as well as color detectors. Temperature control is provided through flowing fluid leading to the potential for rapid temperature variations which would be lethal to living tissues. Furthermore, the Guinn et al. system offers no protection to the operator from accidental exposure to infectious or toxic materials.

U.S. Pat. No. 4,446,229 to Indech discloses a method of tissue growth wherein fetuses are transplanted to a unit which circulates blood through an artificial vasculature lung and kidney apparatus. The unit is subjected to ultraviolet light from an integral source to provide sterilization. Such devices usually generate ozone which is toxic to the living tissues. However, Indech fails to disclose any provision for removal of ozone which is generated. A base tissue of non-immunoreactive mesentery is presented to the transplant to which an outgrowth of vasculature is encouraged. Indech claims a method for aseptic addition of materials into the system for testing purposes with respect to the implanted tissue or fetus. Indech fails to disclose methods employed to maintain a sterile barrier. The Indech device is only applicable concerning tissues, embryos and fetuses which are competent to form vasculature tissue denovo.

U.S. Pat. No. 4,889,691 to Argentieri discloses a modular tissue superfusion chamber including a receptacle support having a recess for receiving one of a plurality of modular bath containers which hold tissue samples being tested for electrophysiological responses to commands. While the receptacle support includes a Peltier heater therein, the tissues are exposed to the environment and, as such, may not be isolated from potential contamination.

U.S. Pat. No. 4,680,266 to Tschopp et al. discloses a cell culture chamber with means for automatic replenishment of nutrient. Tschopp et al. disclose a device which may be utilized for carrying out or implementing biological experiments under zero gravity conditions. While this aspect is in common with the teachings of the present invention, the present invention differs from the teachings of Tschopp et al. in many respects. Firstly, the Tschopp et al. device is non-mechanical in nature and relies on osmotically pumped fluid moving through channels drilled into the body of the apparatus, passing over attached cells which reside in a cavity and grow on removable glass windows. The spent media is conveyed into the general cavity of the apparatus. The unit is not self-sustaining and must reside in an incubator so that thermal and atmospheric conditions may be regulated. The device of Tschopp et al. may not be replenished or serviced and cannot be sampled during the course of an experiment.

U.S. Pat. No. 3,065,148 to Ferrari, Jr. discloses a method and apparatus for use in conducting studies on cells. The Ferrari, Jr. device uses very short-term exposure of the cells to test materials and relies upon changes in the rate of carbon dioxide evolution by the cells as an indicator. The individual cells may be recovered in this test scheme and effluent may be fractionated to test for the release of recognized indicators of cell stress and toxic response. Since most cells in the mammalian body are anchorage-dependent, this testing scheme is of severely limited utility in current state of the art laboratories. The Ferrari, Jr. device may not be effectively used for toxicity and carcinogenicity screening.

SUMMARY OF THE INVENTION

The present invention relates to an automated system for culturing and testing of cells and tissues. The system is microgravity-adapted and provides a compact, full function growth and experimentation platform for the culture and testing of microorganisms, plant cells and cells derived from animal tissue sources. The system is compatible with both suspended cell ferments and anchorage-dependent cell production either on hollow fibers or microcarriers.

The inventive system provides two aseptic containment barriers to protect workers from accidental escape of noxious or infectious fluids while affording a fully controlled thermal and gaseous environment for the cultures. The apparatus is attitude independent for operation in conditions of normal gravity and in conditions of weightlessness. Additionally, a prototype of the inventive device has successfully flown on the Space Shuttle and has successfully withstood the stress of orbital launch and recovery while successfully operating during the mission.

If desired, the inventive device may be provided with as many as four levels of containment so that complete isolation from the ambient environment may be assured. The system is designed to be capable of "stand alone" operation for the maintenance of cell growth and production without monitoring, provides an intelligent interface for operator control, has an uninterruptable power supply for added system reliability, incorporates an integral fraction collection facility which eliminates the need for breaking of sterile barriers through sample withdrawal and features a precision metering system for the introduction of controlled volumes of media or media enriched with test materials at known concentrations.

When the inventive device is made of a size occupying a volume of approximately 2 cubic feet, up to 20 culture reactors may be supported in self-contained fashion each containing up to 10,000,000,000 cells for a period of up to 28 days without servicing and replenishment. If desired, the system may be reconfigured to allow extended cycle life when used with fewer than 20 culture reactors.

The inventive system has in-line detectors and monitoring devices allowing continuous assessment of the viability of metabolic state of each cell without the need for invasive procedures. In conjunction with these devices, the system includes computer control allowing adjustment of rates of oxygenation, nutrient feed and operation of heat control to maintain all life sustaining factors well within desired ranges.

More particularly, the present invention includes the following interrelated objects, aspects and features:

(A) In a first aspect of the present invention, in order to completely isolate all functions of the inventive device, up to four levels of containment may be provided. At minimum, three levels of containment are provided including an innermost level of containment comprising multiple independent fluid systems consisting of the cell containing vessels, fluid reservoirs, test material reservoirs, propulsion and metering devices, routing devices, gas exchange devices, spent media sump containers, as well as fraction collecting devices and receiving vessels. The innermost level of containment also includes a single gas environment system consisting of a pressure vessel containing ultra-high purity gas mix, a pressure reduction device or regulator, high efficiency filtering appliances, static routing system which interfaces with the individual fluid systems and individual flow control devices. Outside this innermost level of containment, the next level of containment comprises an outer chamber which receives gas released from the inner level of containment and is fluidly connected with the inner level of containment with a one-way valve serially connected with a filter unit to prevent moisture, infectious agents and aerosols from exiting the inner containment. A third, outer level of containment may be provided to completely isolate the two inner levels of containment from the surrounding environment.

(B) The various components contained within the inner level of containment were broadly listed above. Therewithin, a fluid pathway is provided which provides parallel supply of media, nutrients and chemical agents to the cells contained therein. In one important aspect, the reservoirs of fluid are flexible in nature and are pressurized by surrounding elastic sleeves. Plural pumps are provided to allow the various functions of the fluid pathway to occur including a circulating peristaltic pump having rollers sufficiently wide enough to simultaneously pump fluid through a plurality of parallel arranged flexible tubes. In the fluid pathway are a plurality of parallel arranged bioreactors which receive cells and other living tissues which are to be maintained therein. Fluids which are administered to the bioreactors are oxygenated in a way limiting the possibility of toxic bubbling. The device includes integral computer control for the various valves and pumps in the fluid pathway allowing control of administration of fluids as well as removal thereof.

(C) The innermost level of containment also includes a gas pathway permitting oxygenation of living tissues via the fluid pathway as will be described in greater detail hereinafter. A bottle of pressurized gas including a life sustaining percentage of oxygen is incorporated within the device and various pressure regulators, filters and valves are provided to convey the life sustaining gas within a desired range of pressure and humidity to the inboard oxygenators. As briefly described above, spent gasses from the bioreactors are expelled from the innermost level of containment to the next level of containment via filters and one-way valves. Appropriate sensors are provided within the gas pathway to sense dissolved oxygen and/or acidity so that, responsive to receipt of this data, life sustaining gas may be refreshed.

(D) The bioreactors are mounted within recesses in an aluminum heat sink having a Peltier-type heating/cooling mechanism incorporated therewith. Embedded within the heat sink is a temperature sensor which senses the heat sink temperature and conveys this information to the onboard computer control so that operation of the Peltier heating/cooling device may be controlled responsive to sensing of heat sink temperature. Use of a metal heat sink is an advance in systems of this type because (1) it prevents rapid temperature changes which are potentially life threatening and (2) it allows accurate, consistent temperature control even under zero gravity conditions. The Peltier device may heat or cool depending upon the polarity of electrical connection. Under computer control, this polarity may be adjusted and the unit itself may be pulsed on and off at a desired frequency to provide accurate temperature control within $\frac{1}{2}°$ C.

(E) The inventive system has a built-in onboard electronic system for controlling all internal functions. The electronic system includes a master computer driving an LCD display and having a removable keypad to input data and instructions. The master computer controls a plurality of digital controllers each of which has specific controlling functions within the entire system. For example, one digital controller may be provided to control all functions of the gas pathway while another digital controller may be provided to control all functions of the fluid pathway. Still another digital controller may be employed for thermal regulation while another digital controller may be provided to control administration of drugs or other substances and retrieval of data resulting from such administration.

(F) In order to render the present invention completely self-sustaining and independent for long periods of time, a built-in power supply is provided which includes main batteries, back-up batteries as well as interface allowing connection to external power supplies. If the external power supplies fail, the internal back-up and emergency systems instantaneously take over providing uninterrupted power supply to the various systems and sub-systems of the inventive device.

As such, it is a first object of the present invention to provide a system for automated culturing and testing of cells and tissues.

It is a still further object of the present invention to provide such a device including up to four levels of containment to completely isolate the inner workings of the inventive device from the surrounding ambient environment.

It is a still further object of the present invention to provide such a device having an independently controlled fluid pathway allowing supply of nutrients and other media to living cells and tissues.

It is a still further object of the present invention to provide such a device with an independently operable gas pathway providing life sustaining gasses to living cells and tissues while exhausting spent gasses and waste products from the bioreactors while maintaining venting of such spent gasses and waste products through the outer levels of containment of the device to the ambient environment by means of a positive pressure gradient from inside to out. It is a still further object of the present invention to provide such a device with thermal regulation which is operable both in the influence of gravitational fields and in zero gravity.

It is a still further object of the present invention to provide such a device having a built-in computer control allowing monitoring of all system aspects and functions.

It is a still further object of the present invention to provide such a device which may be operated completely independently of outside involvement including the provision of an independently operable power supply and back-up power supply.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 5:
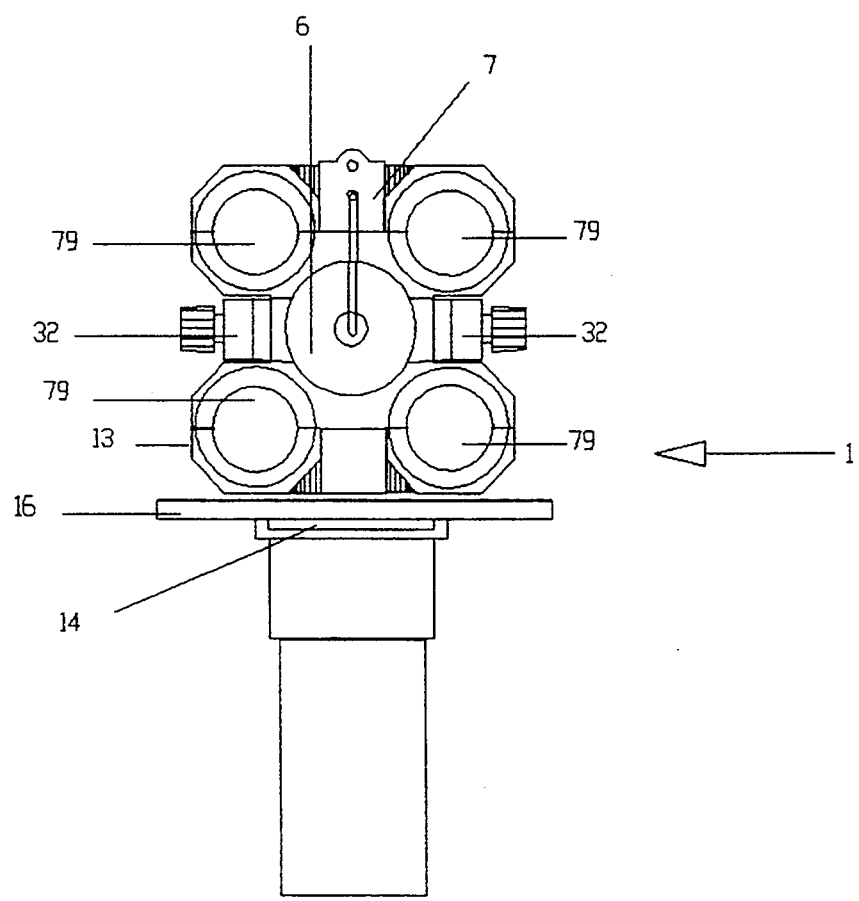
FIG. 5 shows a view from the left-hand side of the rail assembly.
Figure 6:
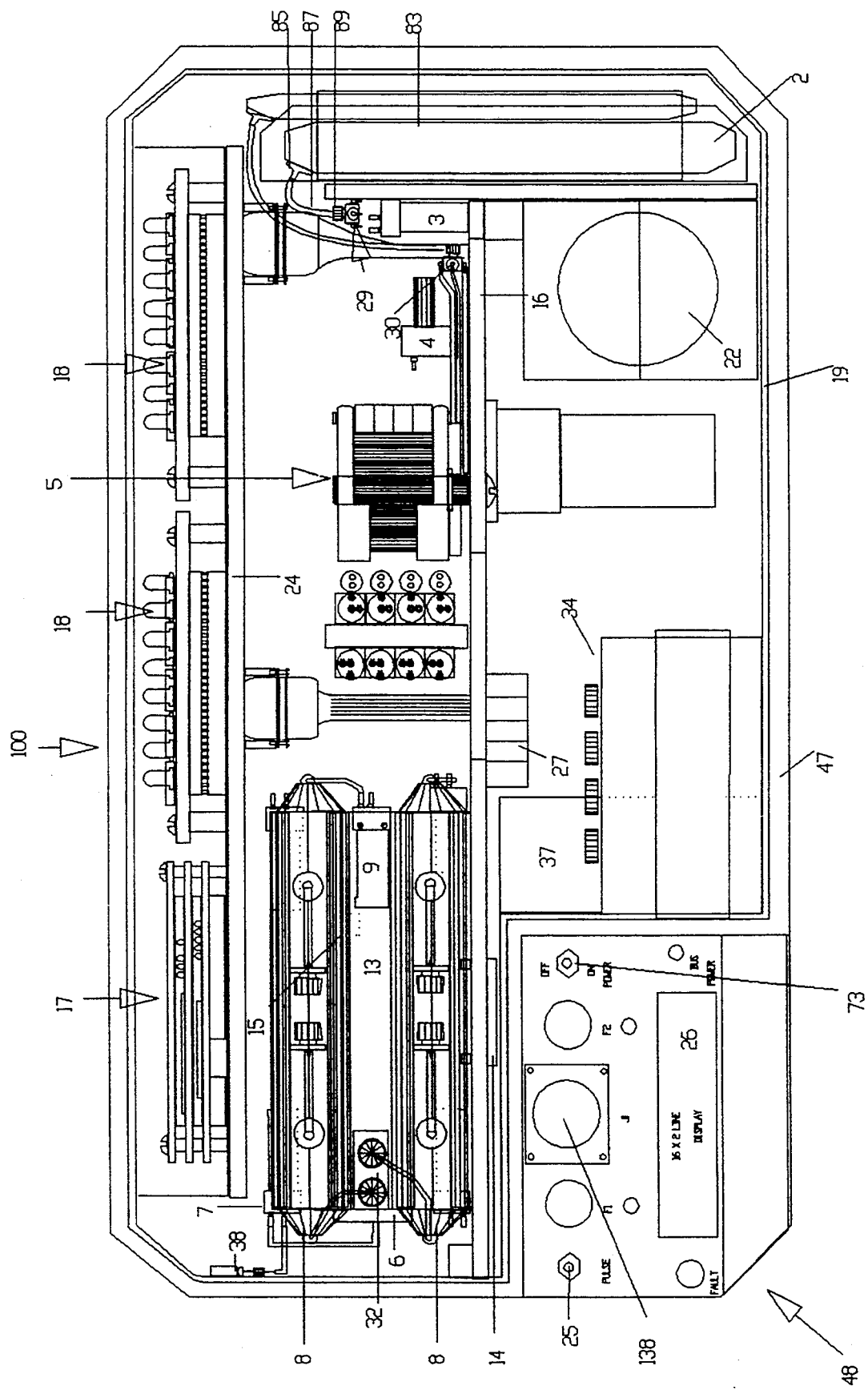
FIG. 6 shows a front view of the present invention with portions broken away to show detail.
Figure 7:
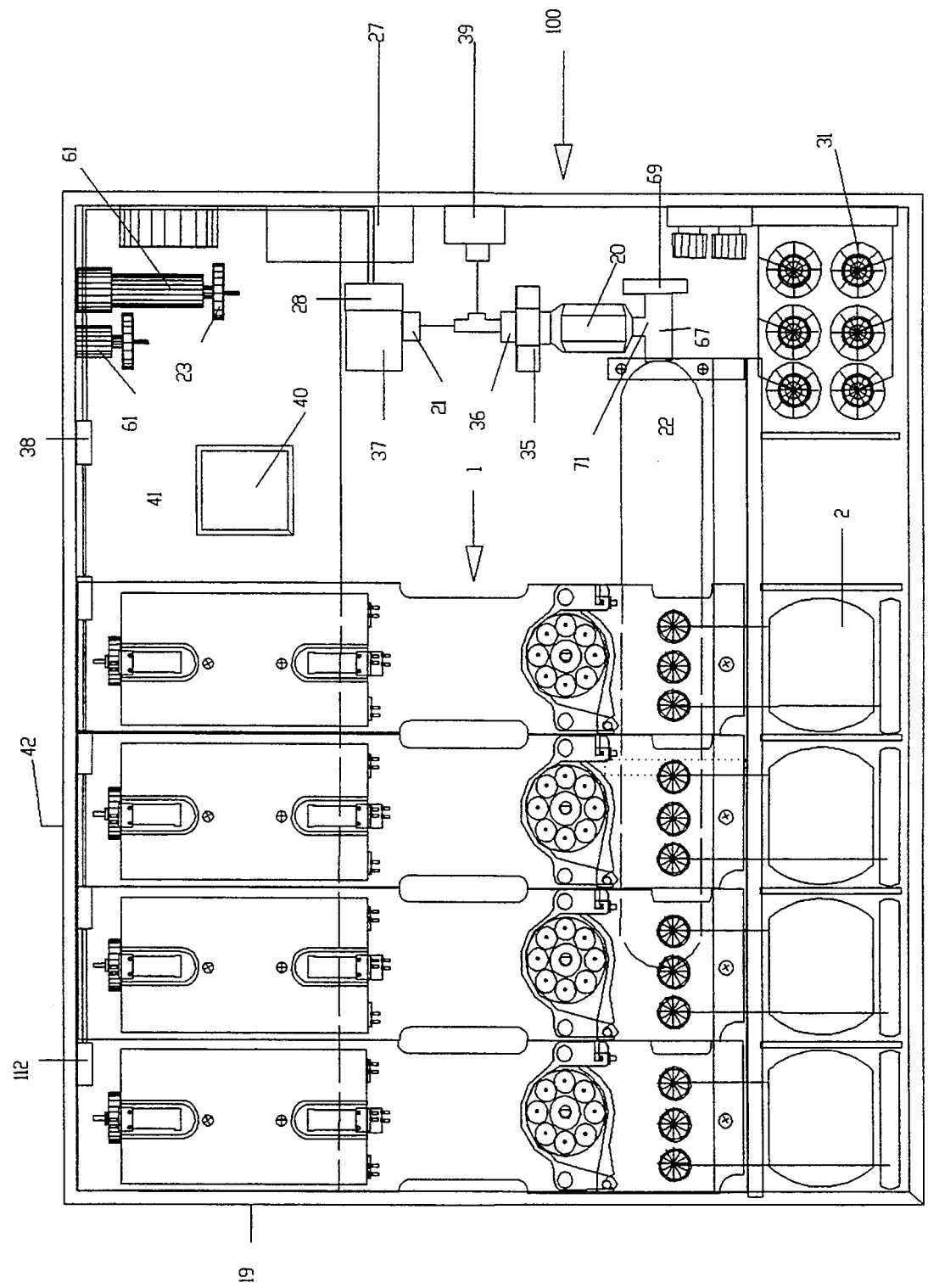
FIG. 7 shows a top view of the present invention with portions broken away to show detail.

Reference is first made to FIGS. 6 and 7 which show front and top views, respectively, of the present invention, as generally designated by the reference numeral 100. With reference to FIGS. 6 and 7, it is seen that the heart of the present invention consists of a plurality of rail assembly means generally designated by the reference numeral 1 and which will be described in greater detail hereinafter with reference to FIGS. 1-5.

Figure 17:
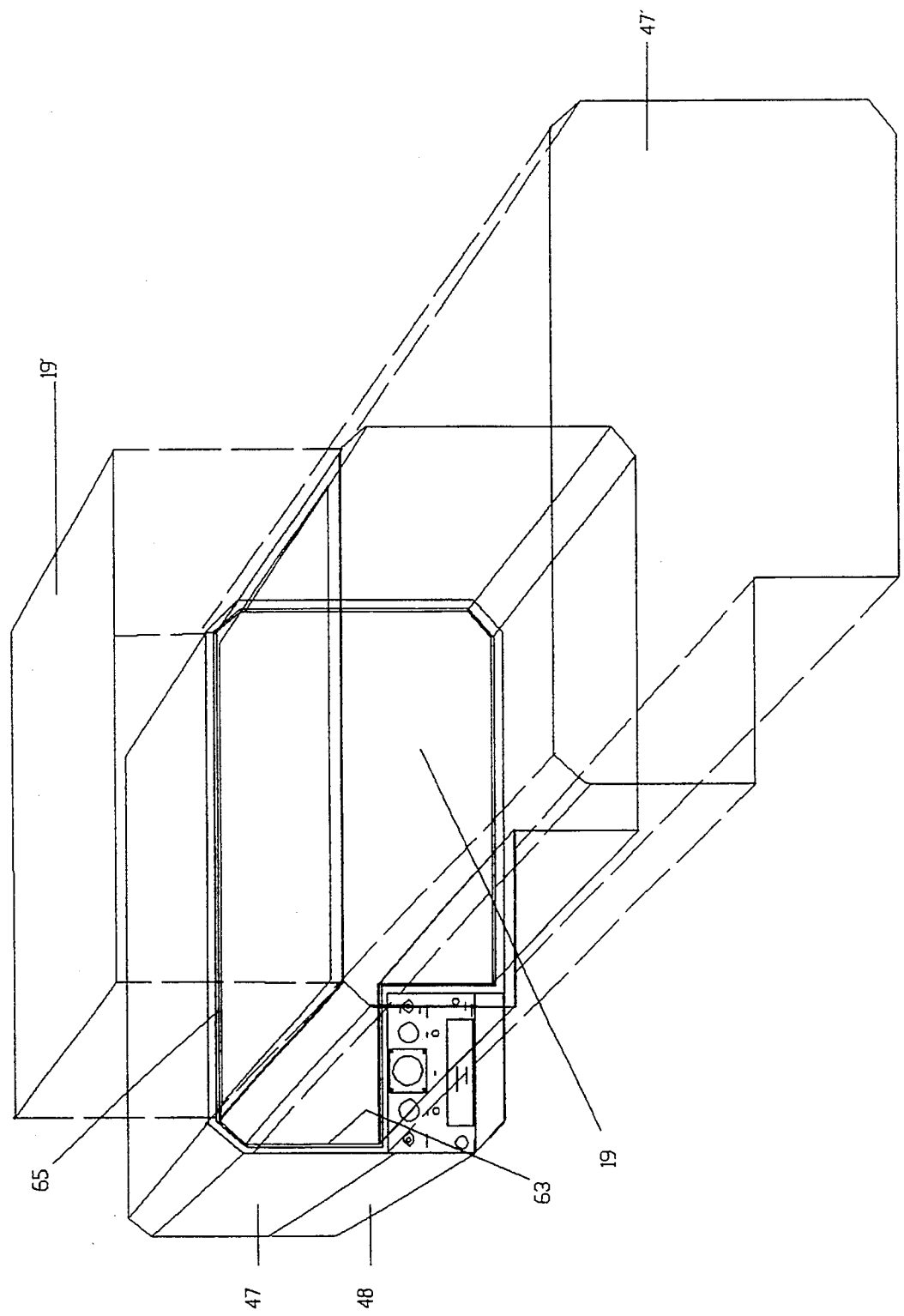
FIG. 17 shows an exploded perspective view of the inventive device depicting the levels of containment thereof.

While the present invention may be provided with four levels of containment, for ease of understanding, only three levels of containment are shown. In this regard, with reference to FIGS. 6, 7 and 17, it is seen that the inventive device 100 includes a third level of containment comprising an outer casing 47 preferably made of a strong, lightweight metal such as, for example, aluminum and which provides the outer containment. A second level of containment is provided by an inner containment vessel 19 having a sealed chamber in which is contained the first level of containment consisting of liquid or fluid pathways, gas pathways and thermal regulation as will be described in greater detail hereinafter. In addition, if desired, electrical circuitry may be provided within the inner containment vessel 19 but in a separate sub-chamber sealed from the other sub-systems contained therein to avoid corrosion or other contamination. As shown in FIG. 17, the inner containment vessel 19 is sealed from the outside and has an access cover 19'. While the inner containment vessel 19 is sealed from incursion of any gas or substance from the outside, relief valves 61, to be described in greater detail hereinafter, allow venting of gasses from within the inner containment vessel 19 to the space surrounding the inner containment vessel 19 and within the outer containment 47. As also shown in FIG. 17, the outer containment 47 has a front panel 47' which may be placed over the front opening 63 thereof and, in conjunction with the resilient peripheral seal 65, may hermetically seal the outer containment 47. Also contained within the inner containment vessel 19 are a digital computer controller 17 as well as a motor, solenoid and heater driver board 18. As noted above, if desired, these electronic components may be contained within a separate sub-chamber within the inner containment vessel 19.

Reference numeral 31 refers to a plurality of test material reservoirs which, as the name suggests, are provided with test materials which may be selectively pumped into the bioreactor means consisting of the bioreactors 8 in a manner to be described in greater detail hereinafter.

With reference back to FIGS. 6 and 7, it is seen that within the inner containment vessel 19, a media reservoir/sump bag combination 2 is provided. The reservoir/sump bag 2 is surrounded by an elastic holster 83 which squeezes the flexible reservoir/sump bag 2 so as to provide a positive pressure. Life sustaining gas preferably including some combination of oxygen, nitrogen and carbon dioxide is supplied to the gas pathway from one or more pressurized bottles 22 contained within the inner containment vessel 19. With particular reference to FIG. 7, it is seen that a pressurized bottle 22 has an outlet valve 67 with an actuating handle 69 so that movements of the handle 69 control flow through the outlet nozzle 71. The outlet nozzle 71 is fluidly connected to a proportioning-type pressure regulator 20 which conveys regulated gas through the filter cartridge 35, the filter 36, the filter 21, the humidifier cartridge 37 and the gas enable valve 28. These components will be described in greater detail with reference to FIG. 14.

With further reference to FIG. 7, it is seen that the relief valves 61 may take on diverse configurations in keeping with diverse characteristics. Thus, for example, the valves 61 may be selected to open at differing levels of pressure threshhold. For example, one such valve 61 may be designed to open at $\Delta$ psi above ambient pressure while another such valve 61 may be designed to open at a threshhold of $\frac{1}{2}$ psi above ambient pressure. The valves 61 maintain a pressure in the vessel 19 slightly above ambient pressure to preclude incursion of contaminants therewithin. These are merely examples of the threshholds which may be chosen for the relief valves 61. In any case, the relief valves 61 vent gasses from the inner containment vessel 19 to the space within the outer containment 47.

As shown in FIG. 6, the inventive device 100 may include a power and display module 48 including a control panel pulse switch 25, an external display 26, an on-off power switch 73, a power jack 138, and other desired aspects as shown.

With particular reference to FIGS. 1–5, the specific details of a single rail assembly means such as those depicted in FIGS. 6 and 7 will now be described in great detail.

As shown in FIGS. 1–5, the rail assembly means 1 includes a plate 16 on which all of the mechanical components thereof are assembled. Applicant has found that an aluminum reinforced printed circuit plate is suitable for use as the plate 16 due to its lightweight, strength and corrosion resistance. A support member 77 extends from the plate 16 and carries a series of selector valves 33 and 10 which will be described in greater detail hereinafter. Additionally, extending from the same face of the plate 16 from which supports 77 emanate, a circulating peristaltic pump 5 is mounted. Additional high precision metering pumps 4, for a purpose to be described in greater detail hereinafter, are also mounted adjacent the peristaltic pump 5.

A parallel lumen oxygenator 6 is mounted within the block 13 and, in surrounding relation therearound, four large bioreactors 8 are mounted within recesses in the block 13. These recesses 79 are best seen with reference to FIG. 15.

Figure 1:
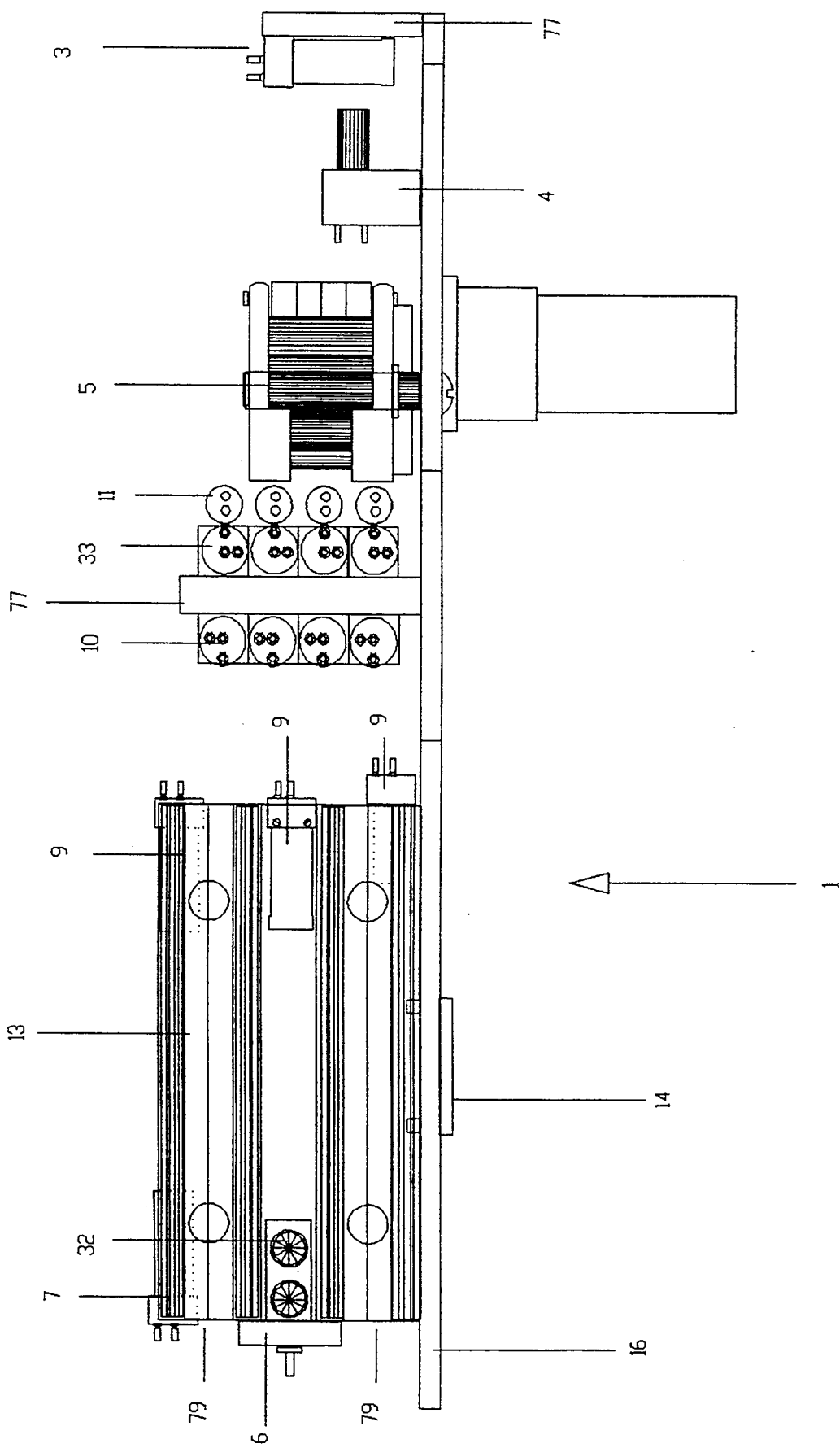
FIG. 1 shows a longitudinal side view of a rail assembly means forming a part of the present invention.
Figure 2:
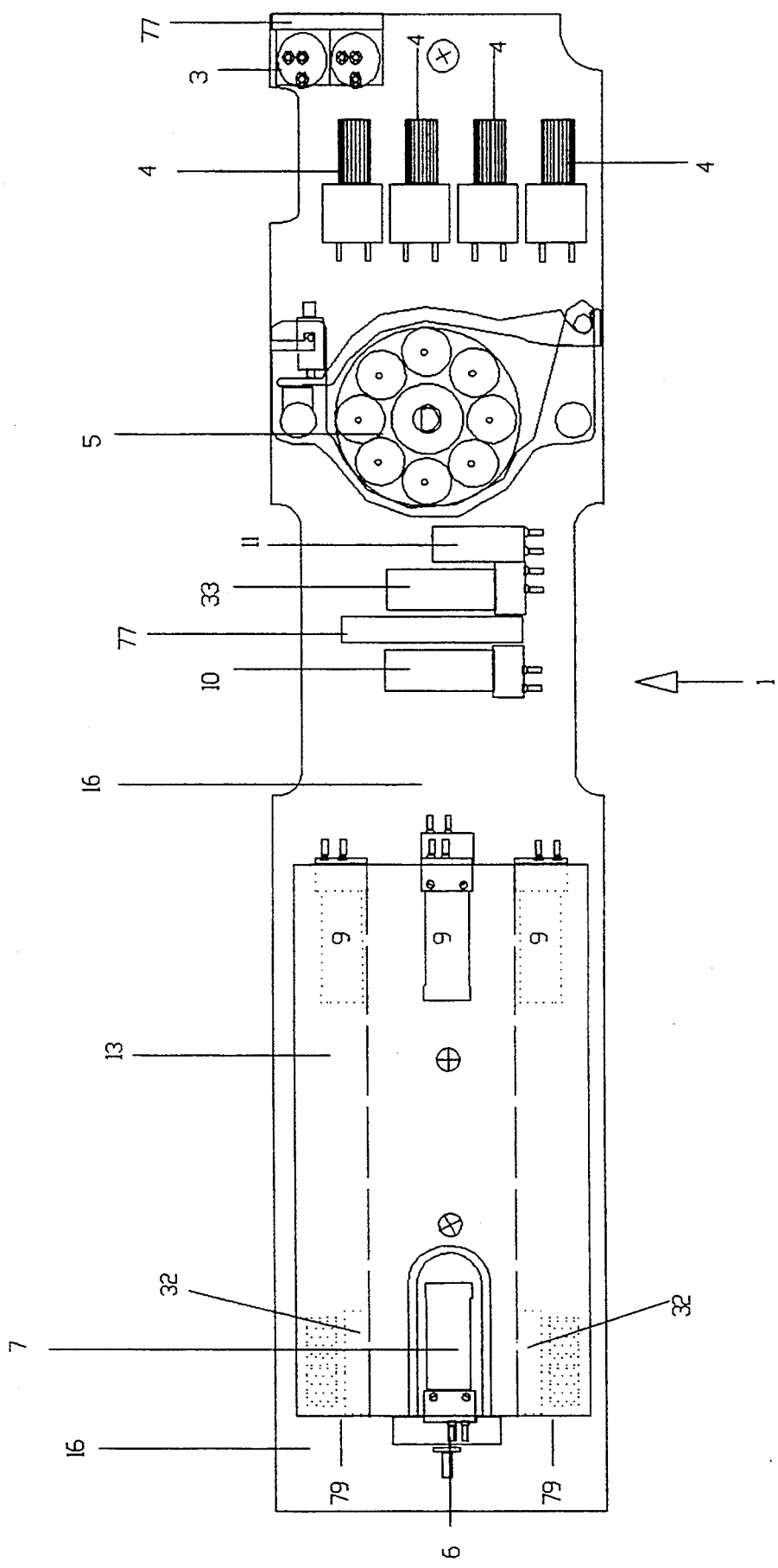
FIG. 2 shows a top view of the rail assembly means illustrated in FIG. 1.
Figure 3:
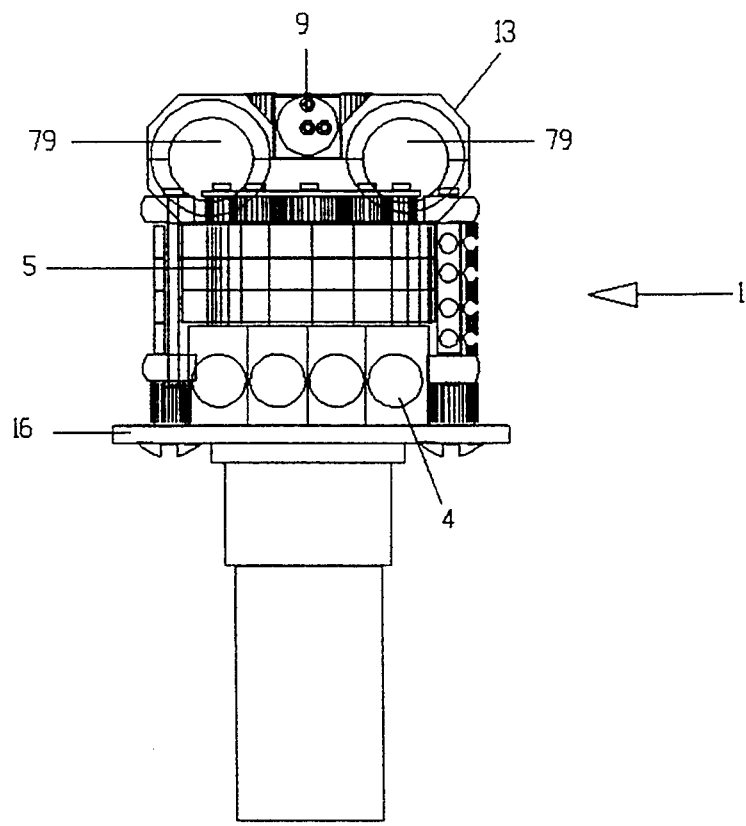
FIG. 3 shows a view from the right-hand side of the rail assembly.
Figure 4:
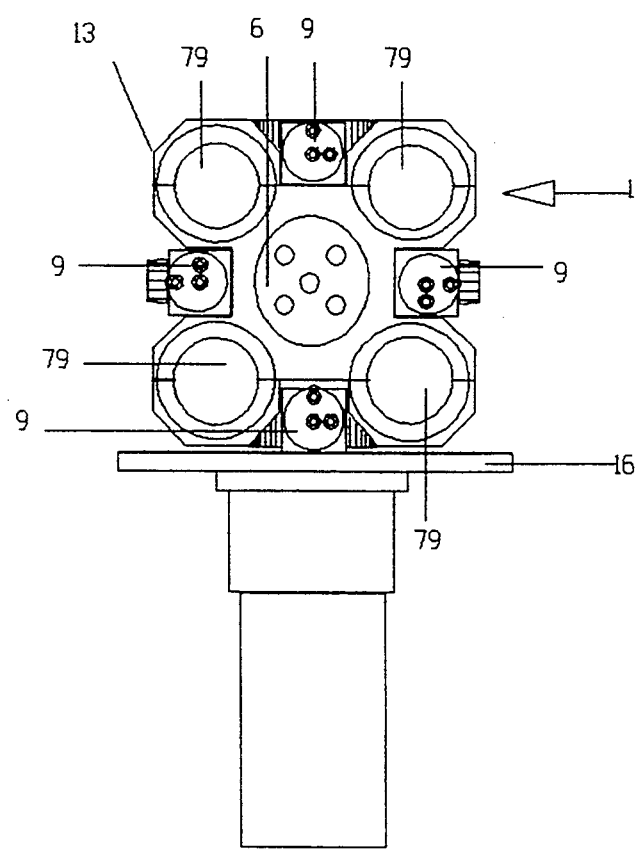
FIG. 4 shows a further view from the right-hand side, but with certain pumps removed to show detail.
Figure 15:
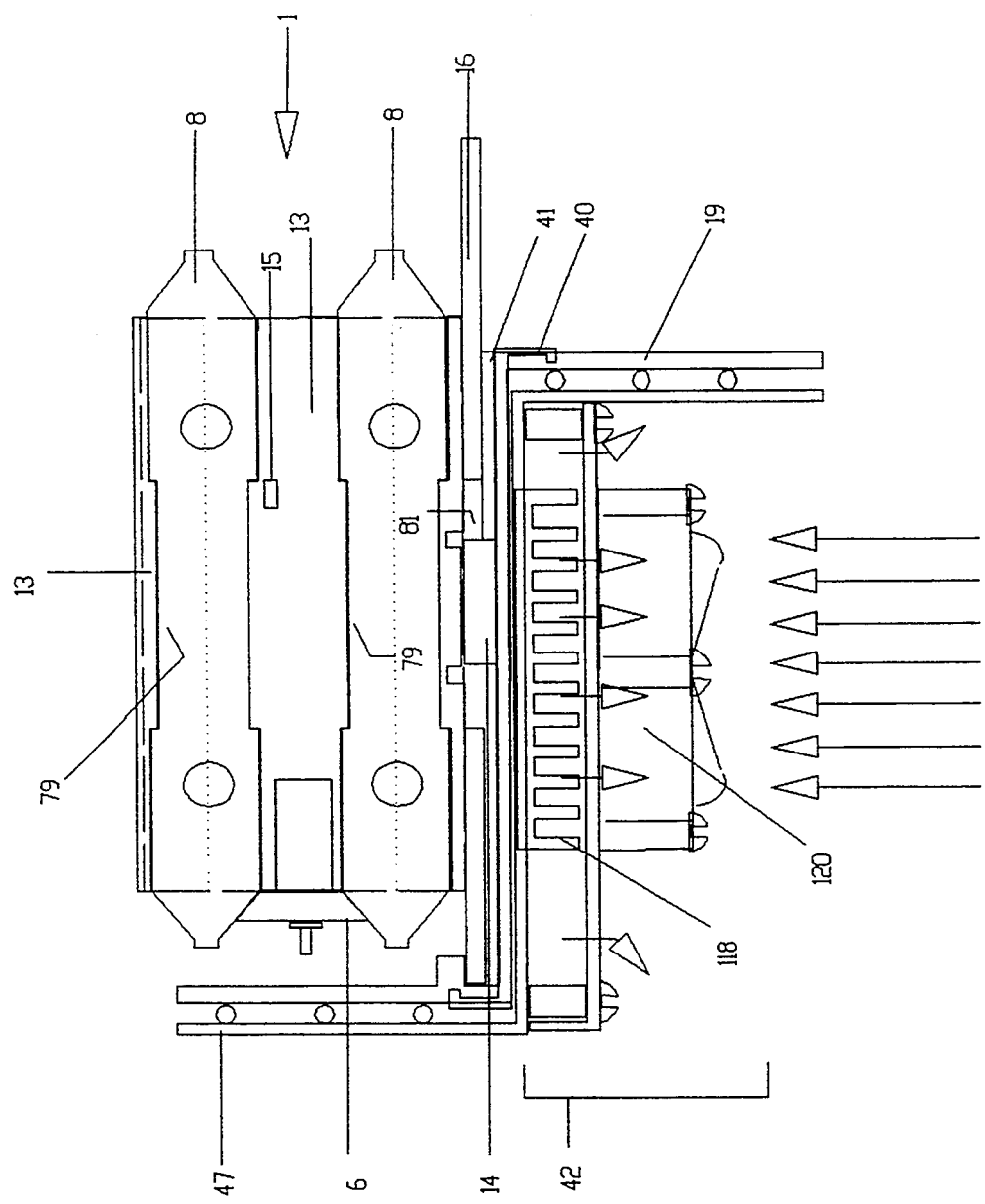
FIG. 15 shows a cross-sectional view along the line XV—XV of FIG. 5, depicting details of thermal regulation.

The block 13 comprises a solid aluminum heat conductor in which the bioreactors reside during operation. As shown in FIG. 1, a Peltier heater/cooler 14 is directly mounted on the block 13. FIG. 15 particularly shows the opening 81 in the plate 16 which allows the heater/cooler 14 to extend through the plate 16 and into direct contact with the block 13. If desired, instead of employing four large bioreactors 8, a larger number of smaller capacity bioreactors may be employed, such as, for example, sixteen small capacity bioreactors (not shown). The valve 7 provided to control gas flow to the parallel lumen oxygenator 6 is best seen with reference to FIGS. 1, 2 and 5. FIGS. 1 and 2 show the port selector valves 9 which control outflow from the bioreactors 8 as well as flow routing valves 10, while FIG. 4 schematically shows one of the selector valves 33, while FIGS. 1, 2 and 5 show open-cell foam bubble arrestors 32 which are provided, as will be described in greater detail hereinafter, to prevent frothing of the media and loss of dissolved proteinaceous components.

The above schematic description of a rail assembly means 1 will become better understood with the following description of the various sub-systems of the present invention.

In this regard, reference is now made to FIGS. 8–13 so that the description of the liquid flow paths of the present invention may be described in great detail.

Figure 8:
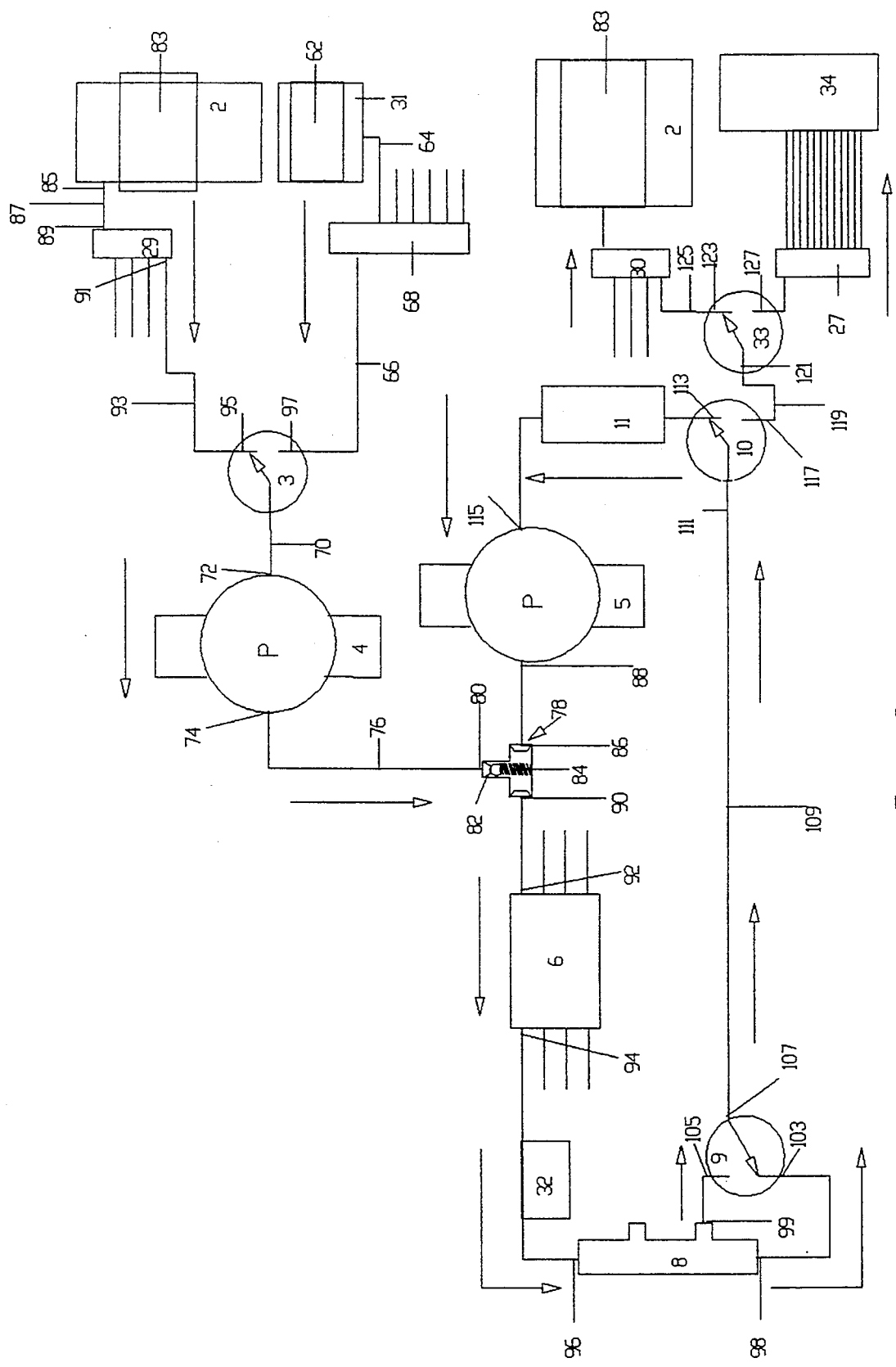
FIG. 8 shows a schematic representation of a typical fluid pathway of the present invention.

With reference, first, to FIG. 8, a general description of the fluid pathway will now be described. As explained above, a single rail may contain as many as sixteen bioreactors 8. As should be understood from the following description, each bioreactor has an individual fluid pathway which is parallel and non-communicating with the fluid pathways supplying and exhausting other bioreactors 8 at least beyond the point of media division manifolds 29 and until the sump collection manifolds 30 are reached. Thus, description of a single such fluid pathway is representative of all of the fluid pathways supplying and exhausting each bioreactor.

With reference to FIG. 8, the flexible plastic bladder 2 is surrounded by an elastic sleeve 83 to pressurize the contents thereof. The bladder 2 is gas impermeable and the elastic holster 83 additionally prevents bubble formation. The bladder 2 has an outlet port 85 to which is coupled a flow passage 87 which is coupled, through suitable coupling means (not shown), with a manifold 29 having a single inlet port 89 and a plurality of outlet ports 91 of which four are shown in FIG. 8. As explained above, downstream of the manifold 29, each individual bioreactor 8 is individually supplied without interconnection with other bioreactors 8. As shown in FIG. 8, the outlet port 91 corresponding to the bioreactor 8 shown therein has a flow passage 93 coupled thereto which supplies media from the bladder 2 to a first inlet port 95 of the three-way solenoid activated selector valve described in the claims as a "second valve means", with the port 95 being that which is normally open when the solenoid (not shown) is deactivated.

In addition, as shown in FIG. 8, a plurality of individual small bladders 31 each provided with individual pressurizing sleeves 62 corresponding to the sleeve 83 are provided. Each bladder 31 may supply a drug, hormone or chemical which is to be used to perform tests in conjunction with living tissue contained within the bioreactor 8. Each bladder 31 supplies the stored substance via a fluid conduit 64 to a manifold 68 which, as should be understood by those skilled in the art, includes an internal valve allowing only one of the bladders 31 to supply fluid to the flow passage 66 which leads to the normally closed inlet port 97 of the valve 3. Thus, the valve 3 may be left in the position shown in FIG. 8 to allow supply of media downstream thereof or, through activation of the solenoid thereof, may be switched to a position allowing supply of substance from one of the bladders 31 therepast.

Downstream of the valve 3, a flow passage 70 supplies fluid to the inlet port 72 of a high precision diaphragm pump 4. The above described aspects of FIG. 8 comprise a first supply means. The outlet port 74 of the pump 4 connects via a flow passage 76 to the inlet port 80 of a T-union 78 which contains a check valve 82 which is biased by the spring 84 in a direction normally closing the port 80 in the absence of applied fluid pressure from the flow passage 76. The T-union 78 also includes a second inlet port 86 which is fluidly connected to the output port 88 of a peristaltic circulation pump 5. As should be understood, the circulation pump 5 includes a plurality of rollers which may be rotated by the pump motor to progressively compress sections of flexible tubing captured therein to permit pumping to take place. The rollers are made sufficiently wide enough to accommodate a number of flexible tubes corresponding to the number of bioreactors 8 included in one rail assembly means 1. The pump 5 comprises a portion of recirculation means permitting recirculation of fluid exiting said bioreactors 8 back to the inlet ports 96 of the bioreactors 8.

The single outlet port 90 of the T-union 78 is fluidly connected to the inlet port 92 of the membrane oxygenator 6. The membrane oxygenator 6, as should be understood, has a tortuously spiraling gas exchange device which receives fluid from the port 92, dilutes the fluid, equilibrates it with gas conveyed as will be described in greater detail hereinafter with reference to FIG. 14, and, also brings the equilibrated fluid to an appropriate life sustaining temperature.

Applicant has found that out gassing is not a concern in the membrane oxygenator 6 since the cellular elements are located external to the capillaries and the capillaries are impermeable to bubbles. If desired, however, in order to be absolutely sure that bubbles which are toxic to sustanation of life are not formed, an open-cell foam bubble arrestor 32 may be provided downstream of the outlet port 94 of the oxygenator 6 to prevent frothing of the media and loss of dissolved proteinaceous components.

With further reference to FIG. 8, properly adjusted media exiting the foam bubble arrestor 32 is supplied at the inlet port 96 of the bioreactor 8. As should be understood, the material flows through the intracapillary space and then diverts and equilibrates with the extracapillary space of the bioreactor 8. The media then exits the bioreactor 8 either via the end port 98 which is directly connected to the intracapillary volume or via a side port 99 which is connected to the extracapillary volume. The route of flow through the bioreactor 8 is determined by a three-way port select valve 9 having a port 103 which is normally open when the solenoid actuator thereof (not shown) is deactivated and a normally closed port 105 which is opened through activation of the solenoid. The valve 9 has a common outlet port 107.

Liquid exiting the common port 107 of the valve 9 is conveyed via the flow passage 109 to the single inlet port 111 of the first valve means comprising a three-way solenoid actuated routing valve 10. The normally open port 113 of the valve 10 supplies fluid from the flow passage 109 to the filter unit 11 which then supplies the fluid to the inlet port 115 of the pump 5 so that the fluid may be recirculated through the closed path shown. When the valve 10 is moved to the normally closed position interconnecting the inlet port 111 with the normally closed outlet port 117, fluid in the flow passage 109 is diverted to the flow passage 119 and thence to the inlet port 121 of the three-way solenoid actuated collection valve 33 (third valve means). The valve 33 has a normally open port 123 which supplies fluid via the flow passageway 125 to the manifold 30 which returns the fluid to the sump 2. When the valve 33 is activated to interconnect the ports 121 and 127, fluid, instead, is supplied to the fraction collection manifold 27 and thence through activation of the fraction collection manifold to a chosen one of a multiplicity of aseptic piston-cylinder collection tubes 34. These tubes may be provided with fixatives or preservatives to stabilize the analyte of interest in the drawn aliquot.

In the preferred modes of operation of the fluid pathway, there are five different combinations of settings of the valves and pumps which are operable to cause various modes of operation of the inventive fluid pathway to occur. Table A shows fluid path logic indicating which components are activated or deactivated. The identifying words for each mode as set forth in Table A will be used in specifically describing the various modes hereinbelow.

TABLE A

| | Fluid Path Logic Table | | | | | | |
|---|---|---|---|---|---|---|---|
| Mode | Valve | 3 | 9 | 10 | 33 | Pump | 4 | 5 |
| Recycle | | 0 | 0 | 0 | 0 | | 0 | 1 |
| Add Media | | 0 | X | 1 | X | | 1 | 0 |
| Add Test Material | | 1 | X | 1 | X | | 1 | 0 |
| Collect Effluent | | X | 0 | 1 | 1 | | 1 | 0 |
| Collect Cells | | X | 1 | 1 | 1 | | 1 | 0 |
| Mode | Valve | 3 | 9 | 10 | 33 | Pump | 4 | 5 |

X = Optional
0 = Off
1 = Energized

Figure 9:
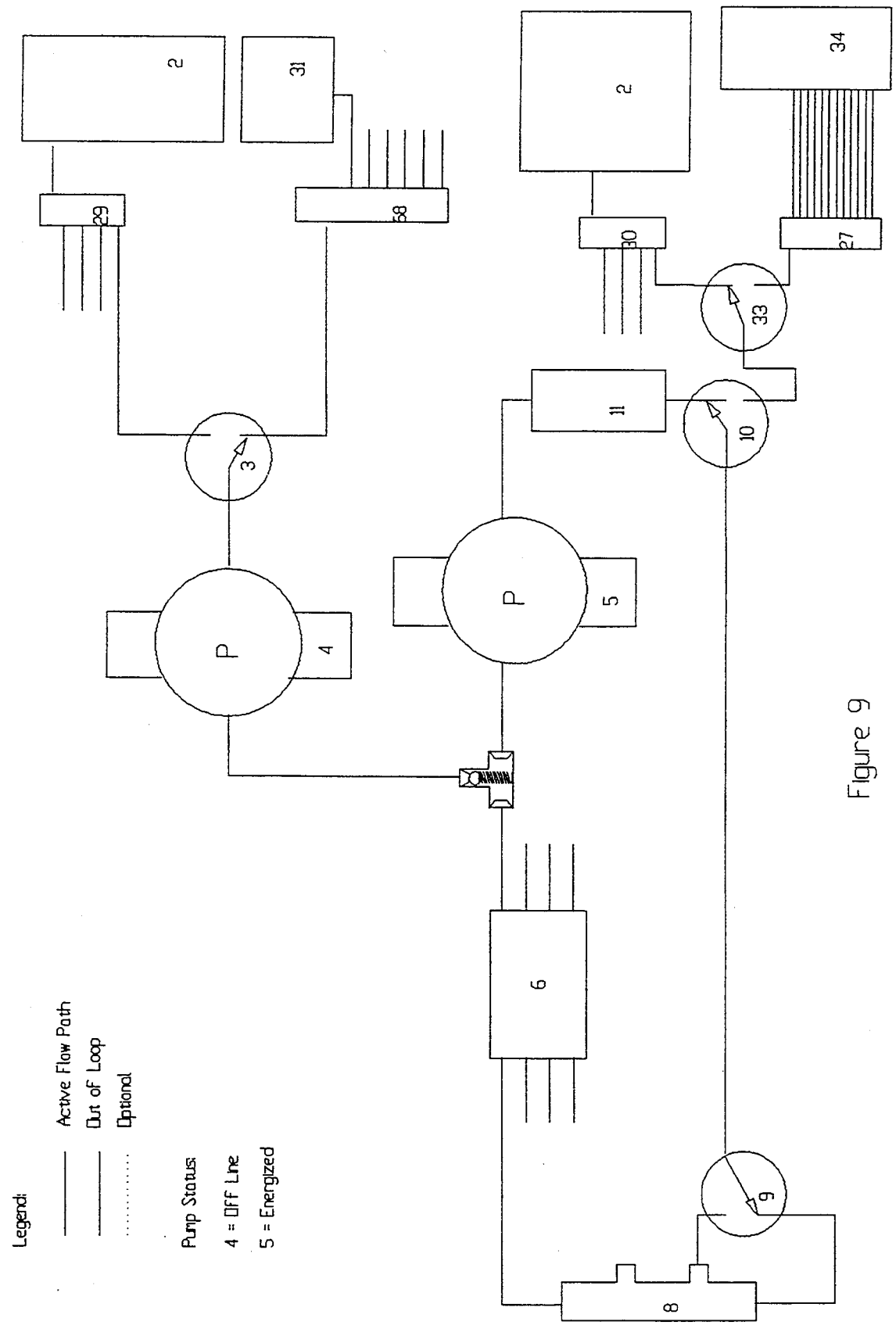
FIG. 9 shows a schematic representation of the fluid pathway in a first configuration thereof.

With reference to FIG. 9, the inventive fluid pathway has been organized in the "recycle mode". In this mode, the valves 3, 9, 10 and 33 are in their de-energized positions, the pump 4 is de-energized and the pump 5 is energized. In this mode, a volume of media is retained within the closed circulation path shown and is repeatedly provided at the inlet port 96 of the bioreactor 8. A mobile fraction is drawn from the outlet 98 of the bioreactor via the valve 9 port 103, is supplied to the port 111 of the valve 10 and exits the valve 10 at the port 113 where it is supplied through the filter 11 to the inlet port 115 of the pump 5. After exiting the pump 5 at the port 88, the media flows through the T-union 78 and enters the membrane oxygenator 6 via the input port 92 thereof. The media is re-oxygenated and brought up to proper temperature and then is applied to the inlet 96 of the bioreactor 8 thus completing the loop.

Figure 10:
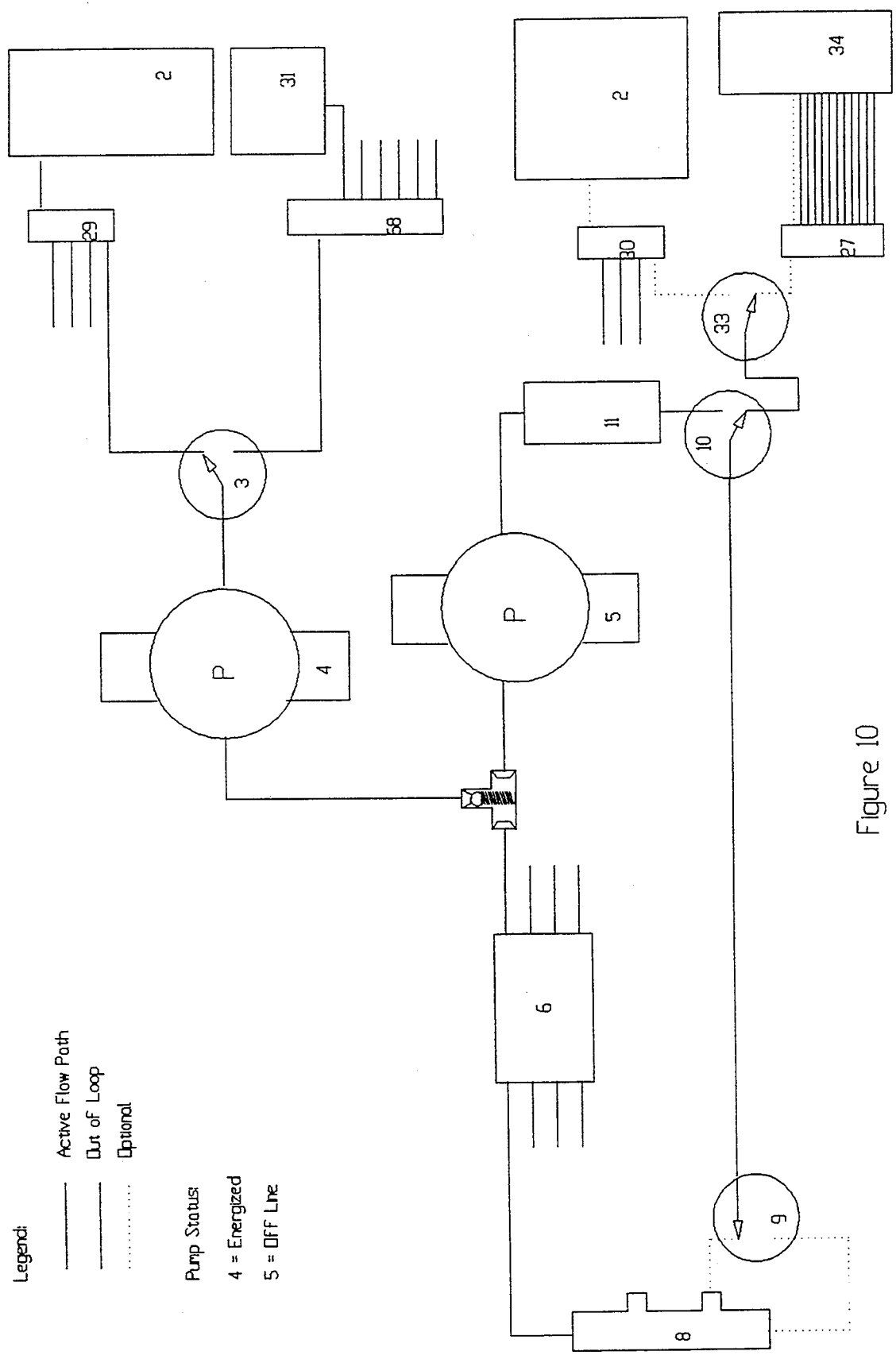
FIG. 10 shows a schematic representation of the fluid pathway in a second configuration thereof.

With reference to FIG. 10, the pumps and valves are organized in a configuration termed the "add media mode". In this mode, with reference to Table A, the valve 3 is deactivated, the valve 10 is activated, the pump 4 is activated and the pump 5 is de-activated. The position of the valves 9 and 33 is at the option of the user. This is because the bioreactor 8 may be evacuated via either port 103, 105 of the valve 9. Furthermore, the valve 33 may be moved to whichever position is desired, depending upon whether fluid is being returned to the sump 2 or is being collected at the collection tubes 34.

In the "add media" mode, a volume of fresh media is introduced into the system and an equivalent volume of spent waste-laden media is removed to either the sump 2 or the fraction collector 34 depending upon the desires and needs of the user. Media is drawn from the reservoir 2 via the manifold 29. The media is conveyed via the selector valve 3 to the operating pump 4 which pumps the fluid through the T-union 78 and thence to the inlet port 92 of the oxygenator 6. The deactivated pump 5 prevents reverse flow through the recirculation line. The media flows through the oxygenator 6 and thence to the bioreactor 8. The media flow may exit from either the end port 98 or the side port 99 of the bioreactor 8 depending upon the desires of the user with the flow traversing the selector valve 9 and being applied to the inlet port 111 of the valve 10 which, as energized, fluidly connects the inlet port 111 with the outlet port 117 thereof supplying fluid to the inlet port 121 of the valve 33. The valve 33 is either activated or de-activated, as desired, to supply the media either to the sump 2 via the manifold 30 or to the fraction collection tubes 34 via the manifold 27. Total fluid circuit volume is unchanged during this mode of operation.

Figure 11:
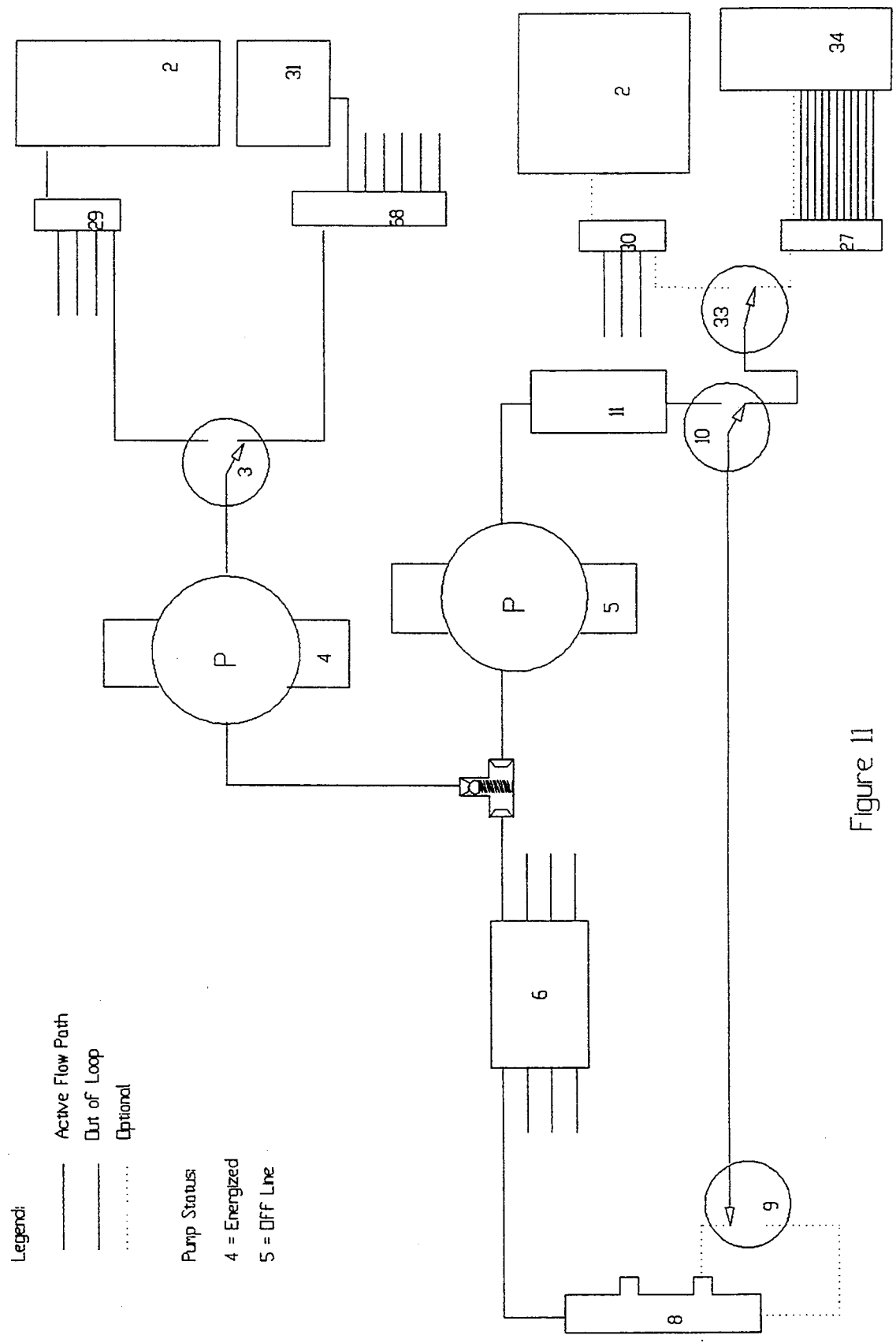
FIG. 11 shows a schematic representation of the fluid pathway in a third configuration thereof.

With reference to FIG. 11, the "add test material" mode will now be described. With reference to Table A, in this mode, the valves 3 and 10 are activated, the pump 4 is activated and the pump 5 is de-activated. The valve 9 is either activated or de-activated depending upon the needs of the user. In this mode, a volume of fluid is withdrawn from one of the test material reservoirs 31 which has been selected through actuation of the rotary manifold 68. The test fluid flows via the energized selector valve 3 from the port 97 to the flow passage 70, thence to the pump 4 and thereafter through the T-union 78 to the membrane oxygenator 6, thence to the bubble arrestor 32 and to the inlet port 96 of the bioreactor 8. Following sufficient addition of test material, the manifold 68 may be moved to a position wherein it may be supplied with plain media to wash all residual material from the flow lines associated therewith in preparation for the next test. If desired, reagents may also be introduced to the system in this manner. Otherwise, this mode operates the same way as the "add media" mode described above.

Figure 12:
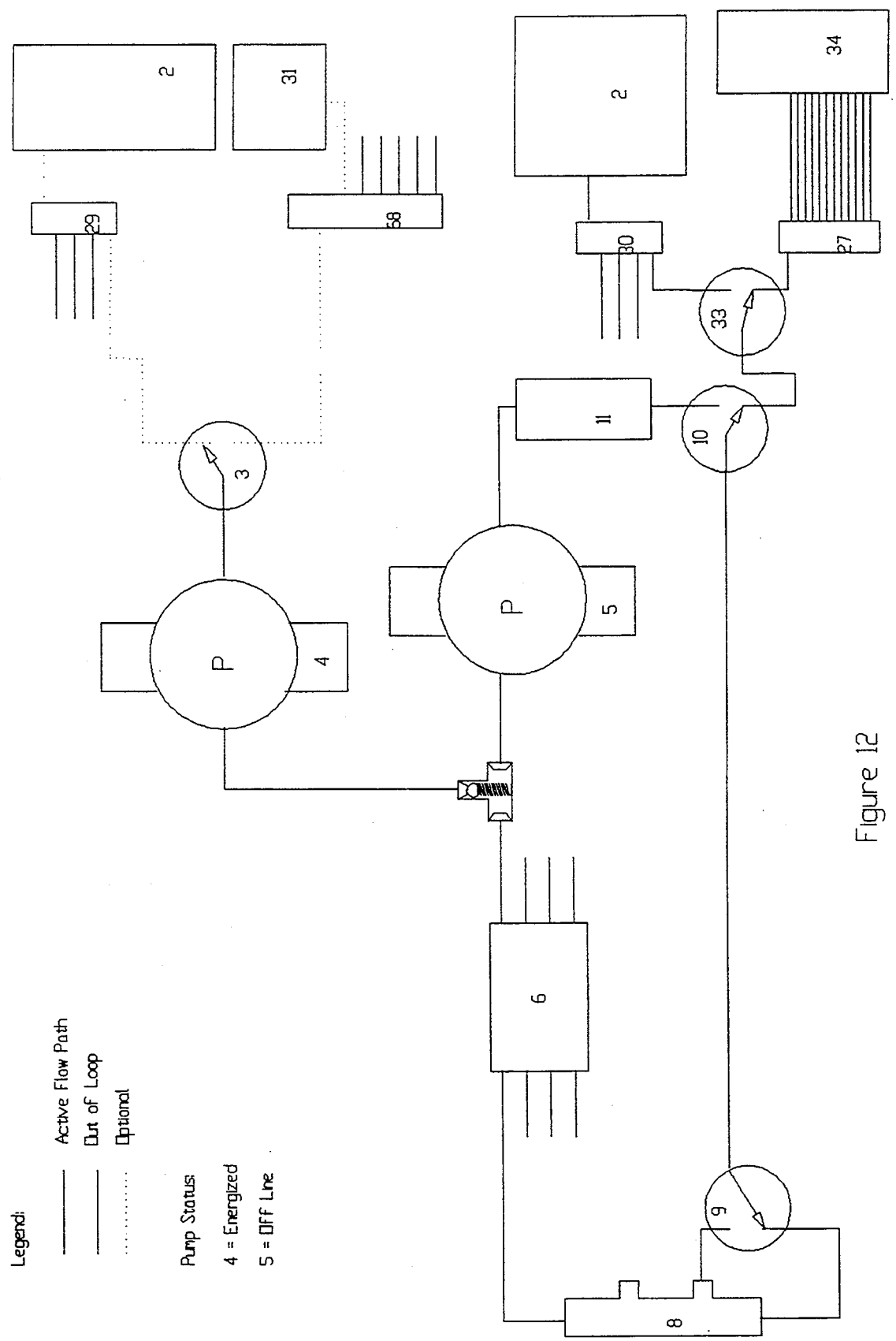
FIG. 12 shows a schematic representation of the fluid pathway in a fourth configuration thereof.

With reference, now, to FIG. 12, a description of the "collect effluent" mode will now be described. With reference to Table A, it is seen that the valve 9 is de-energized, the valves 10 and 33 are energized, the pump 4 is energized and the pump 5 is de-energized. The position of the valve 3 is at the option of the user, depending upon whether the user desires to supply fluid from the media reservoir 2 or from the test material reservoir 31. Fluid flows via the selector valve to the energized pump 4 and into the fluid circuit via the T-union 78. Fluid exiting the bioreactor 8 passes through the de-energized selector valve 9 via the ports 103 and 107 and through the energized selector valves 10 and 33 via the ports 111 and 117 of the valve 10 and via the ports 121 and 127 of the valve 33. The manifold selector switch 27 is temporarily re-positioned to a tap connected to the sump manifold to allow flushing of retained fluid left in the circuit from the last collection into the sump. This volume is dependent upon system geometry but is typically less than 100 microliters. Following this purging, the manifold selector 27 is repositioned and fluid is diverted to appropriate collection tubes 34. In this manner, an aliquot of fluid characteristic of the system charge is obtained. An alternative method for non-random access collection devices is possible in which the selector valve 33 is temporarily de-energized at initiation of collection. This diverts fluid initially located between the valves 10 and 33 to be sent to the sump. In this way, only fluid retained between the valve 33 and manifold 27 is mixed with the sample. The fluid passageway connecting the valve 33 and the manifold 27 is extremely short in length making such mixing extremely minor. This latter explained procedure may be appropriate only when minor contamination of sample with dead volume material is of no concern.

Figure 13:
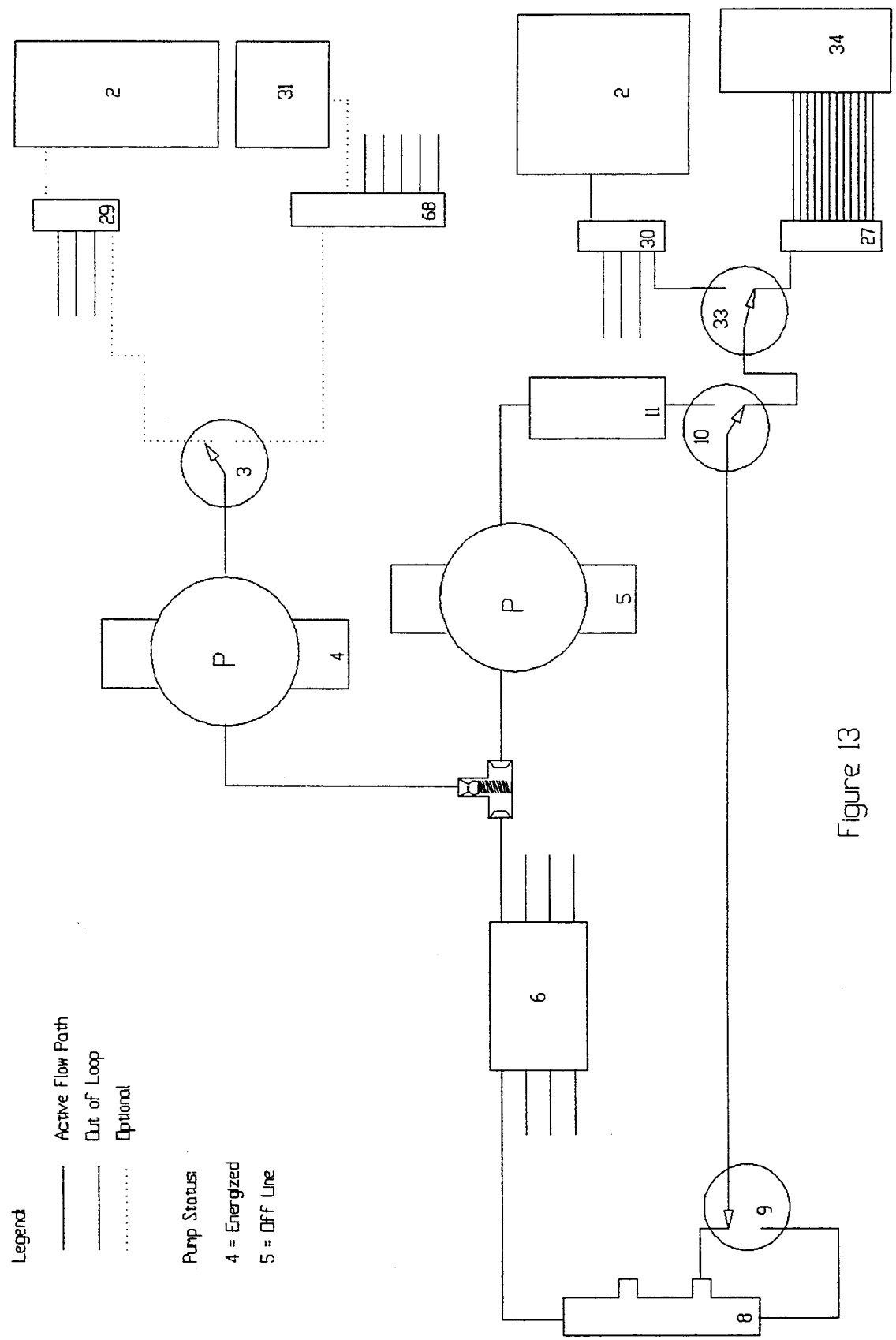
FIG. 13 shows a schematic representation of the fluid pathway in a fifth configuration thereof.

With reference to FIG. 13, the "collect cells" mode will now be explained. With reference to Table A, in this mode, the valves 9, 10 and 33 are energized, the pump 4 is energized and the pump 5 is de-energized. The position of the valve 3 is at the option of the user.

In this mode, the selector valve 9 may be temporarily energized to allow a desired volume of cells on carrier beads to exit the extracapillary space of the bioreactor 8 via the port 99. Following attainment of this sample volume, the valve 9 may be de-energized to prevent further exhaustion of available cell-carrier bead supplies. Temporary re-positioning of the manifold 27 or de-activation of the selector valve 33 is maintained to flush the dead volume of material between the valve 9 and the manifold 27. Thereafter, the selector valve 33 may be energized and the aliquot of cells collected from the bioreactor 8 may be conveyed into an appropriate tube 34 via the valve 10, the valve 33 and the manifold 27. The appropriate tube 34 may contain fixatives and/or preservatives previously added at the discretion of the user.

Figure 14:
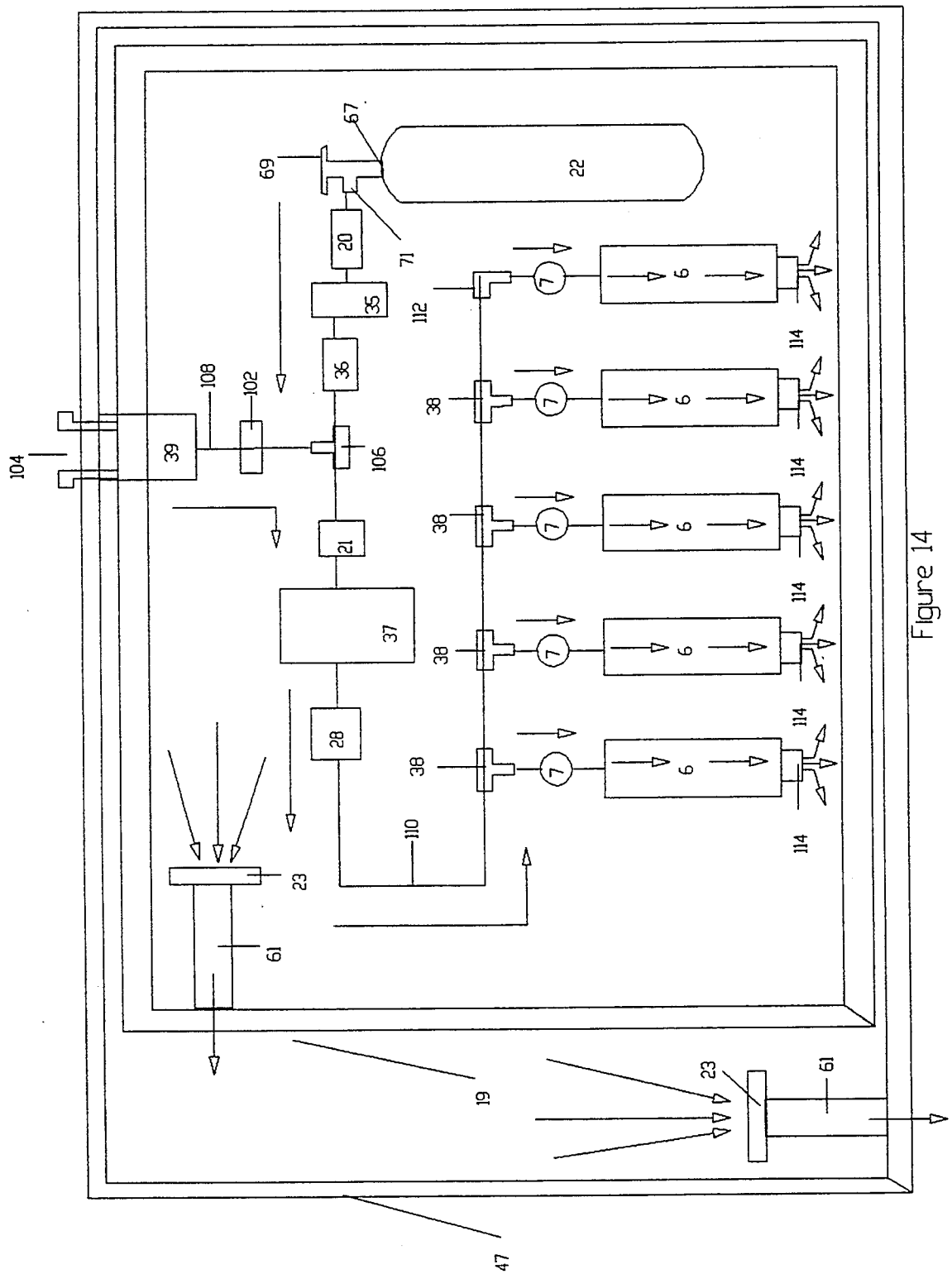
FIG. 14 shows a schematic representation of the gas pathway of the present invention.

With reference, now, to FIG. 14, in particular, an explanation of the gas pathway of the inventive system 100 will now be described in greater detail. As shown, the main portions of the gas pathway are contained within the inner chamber 19. As shown in FIG. 14, pressurized gas is contained within a bottle 22 which carries a valve 67 having an actuating handle 69 and an outlet nozzle 71 fluidly connected to a pressure regulator 20. The pressure regulator 20 reduces gas pressure to working levels whereupon the gas passes through an activated charcoal/molecular sieve cartridge 35 designed to remove potential organic contaminants. Thereafter, the gas mixture is passed through a 70 micron sintered bronze particulate filter 36 which protects the system from dust which might be generated within the cartridge 35.

As also shown in FIG. 14, supplementary gas input is permitted via a quick disconnect coupling 39 which extends through the containment 19 as well as the outer wall 47 at an access opening 104. The coupling 39 is fluidly connected to an unvalved T-union 106 via a flow passageway 108 and a one-way check valve 102 precluding reverse flow out the coupling 39. In the preferred embodiment, the check valve 102 is designed to open at a pressure greater than 10 psi above ambient.

Downstream of the T-union 106, a 0.2 micron HEPA filter 21 is provided to remove any residual particulates which might happen to pass through the particulate filter 36. At this point, the gas mixture is as clean as possible and is thereafter passed through a humidifier cartridge 37 in which water vapor equilibrates across a membrane and saturates a charge of gas passing therethrough. Downstream of the humidifier cartridge 37, a valve 28 is provided which may be remotely controlled by the master computer as pre-programmed. Downstream of the valve 28, a flow passage 110 conveys the gas mixture to a series of serially disposed T-unions 38 along with an L-shaped union 112 at the termination of the flow passage 110.

Each of the unions 38, 112 conveys the gas mixture to a high pressure valve 7 which may have a solenoid actuator remotely controllable by a digital computer controller, as will be described in greater detail hereinafter. Downstream of each valve 7 is an individual membrane oxygenator 6.

Figure 18:
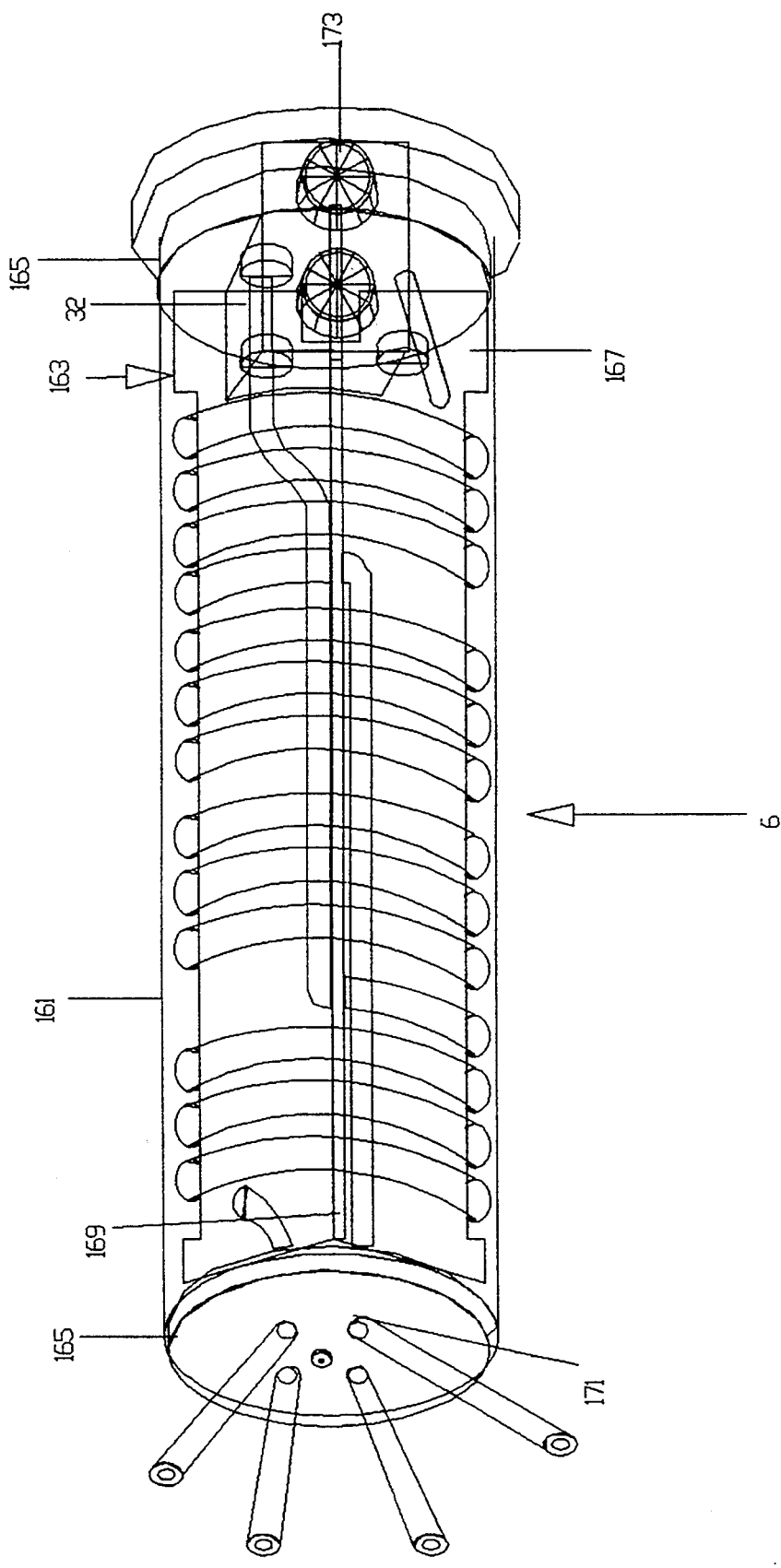
FIG. 18 shows a cross-sectional view through a membrane oxygenator of the present invention.

The oxygenation means comprises an oxygenator 6 (FIG. 18) and consists of a cylinder 161 of acrylic or polycarbonate tubing of defined diameter. A removable insert spool 163 with one end cap 165 the size of the inner diameter of the cylinder and the other end having a flange to allow only partial insertion into the cylinder constitute the fluid path proper of the oxygenator. The insert spool is composed of two interlocking plates 167, 169 which form an X-shaped cross-section. Appropriate holes and undercuts allow threading of the exchange membranes and permit alignment of input and outlet ports for unambiguous hook-up.

The input end cap is provided with transit holes 171, 173 through which the membranes pass and are sealed with potting compound. Hose barb connectors are attached to the input side of the oxygenator. The flanged end may be beveled, for example, 22° and may be provided with threaded luer lock connectors for economy of space when bubble arrestors are not used. This configuration allows removal of the unit without the total disassembly of a rail assembly means 1. Each membrane oxygenator 6 is fully autoclavable. The inventive membrane oxygenator 6 is unique in providing discrete paths for parallel simultaneous treatment of the liquid content of the several individual paths on a rail assembly means 1. The gas is introduced in a counter current manner with respect to the flow of media in order to achieve maximum efficiency of gas uptake. Dissolved oxygen and/or acidity are sensed by indwelling detectors as well as flow cell pH electrodes. On the basis of these data, software controlled decisions are made to refresh the volume of gas in an oxygenator 6.

Alternatively, timed introduction of fresh gas to the volume of the oxygenator is available for maintenance of the acidity of the media. While commercial membrane oxygenator units may also be utilized in conjunction with the present invention, the improvements over known oxygenators which are included in the inventive oxygenator 6 render it extremely advantageous in the present invention given the requirements of the present invention for sterility, complete oxygenation of media, resistance to bubble formation, etc.

In each oxygenator, maximum transfer of gas to media occurs. Gas which is not transferred to media is released from each oxygenator 6 via an outlet check valve 114 attached thereto and into the general chamber defined by the containment vessel 19. This chamber fluidly connects with the chamber formed by the outer containment 47 via a series of check valves 61 protected by filter units 23, such as, for example, a 0.22 micron filter unit which effectively prevents moisture, infectious agents and aerosols from exiting the inner containment 19. Two such cascaded check valves 61 are best illustrated in FIG. 7 and, for example, may be designed to open at ⅓ psi above ambient and ½ psi above ambient, respectively. This configuration maintains the chambers defined by the containments 19 and 47 at a positive pressure above ambient, thereby preventing incursion of contaminants.

All of the components of the gas pathway as particularly illustrated in FIG. 14 are critically cleaned of all solvents, lubricants and coatings prior to assembly so that essentially pure gas may be provided to the living tissues contained within the bioreactors 8.

With reference, now, to FIG. 15, the specific means for thermal regulation comprising thermal control means will now be described. As shown in FIG. 15, and as described hereinabove, the casing 13 has a plurality of recesses 79 with each recess being sized to snugly receive a bioreactor 8 therewithin. The casing 13 is made of a material such as, for example, aluminum and comprises a solid conductive heat sink. As shown, a single membrane oxygenator 6 is provided for each casing 13 and serves to supply life sustaining gasses to all of the bioreactors 8 contained within the casing 13.

As also shown in FIG. 15, the plate 16 of the rail 1 has an opening 81 therethrough which allows insertion of a Peltier-type heating/cooling unit 14 so that the unit 14 is in direct physical engagement with a wall of the casing 13, as shown. As is known, Peltier heating/cooling units consume low amounts of power. In the present invention, each Peltier unit 14 is operated in a pulsing on/off manner with fine control being exerted by controlling the rate of switching on and off. This control is exercised by a digital controller incorporated in the present invention and as will be described in greater detail hereinafter. A sensor 15 is buried within the casing 13 and senses casing temperature, conveying this information to the digital controller so that, under software control, the digital controller can control activation and de-activation of the Peltier device 14. The temperature sensor 15 may be a thermistor or a dedicated integrated circuit. As should be understood, an A/D converter is interposed between the temperature sensor 15 and the digital controller.

As should be understood from the above explanation, output from the sensing element is applied to the digital controller via the A/D converter. In accordance with software preprogramming, evaluation is made of thermal data and, responsive to such evaluation, the Peltier unit 14 is operated to maintain the temperature of the casing 13 within a narrow temperature range conducive to maintenance of living tissue viability.

As is known, the direction of heat conduction in a Peltier unit is controlled by the polarity thereof. Thus, in one direction of polarity, the Peltier unit 14 will supply heat to the casing heat sink 13. By reversing the polarity of the Peltier unit 14, heat may be removed from the casing heat sink 13.

As shown in FIG. 15, and as explained above, the Peltier unit 14 extends through an opening 81 in the plate 16 and is in direct engagement with the casing heat sink 13. The opposite face of the Peltier unit 14 engages a metallic sub-plate 40 designed to assist in maintaining radiation of energy from the Peltier unit 14 toward the casing heat sink 13. Additionally, all non-contact surfaces of the casing heat sink 13 are meshed with an insulator such as, for example, metallized MYLAR which rejects greater than 80% of heat which would attempt to transfer therethrough. Through the use of the sub-plate 40 and the insulator 41, thermal short circuiting is prevented. Transfer of heat through the various levels of containment is by direct metal to metal contact aided, where appropriate, through application of heat sink compound. As shown in FIG. 15, a finned heat exchanger 118 is provided and is located adjacent a ventilation fan 120 which is controlled by the digital controller as will be explained in greater detail hereinafter. The region designated by the reference numeral 42 in FIG. 15 may be provided with appropriate filters, if desired, to purify any air which is being moved by the ventilation fan 120.

The solid metal heat sink 13 is advantageous for many reasons. Firstly, this medium prevents rapid temperature changes which can be life threatening. Additionally, the solid material thereof permits effective heat transfer even in zero gravity conditions. Other advantages also exist.

Figure 16:
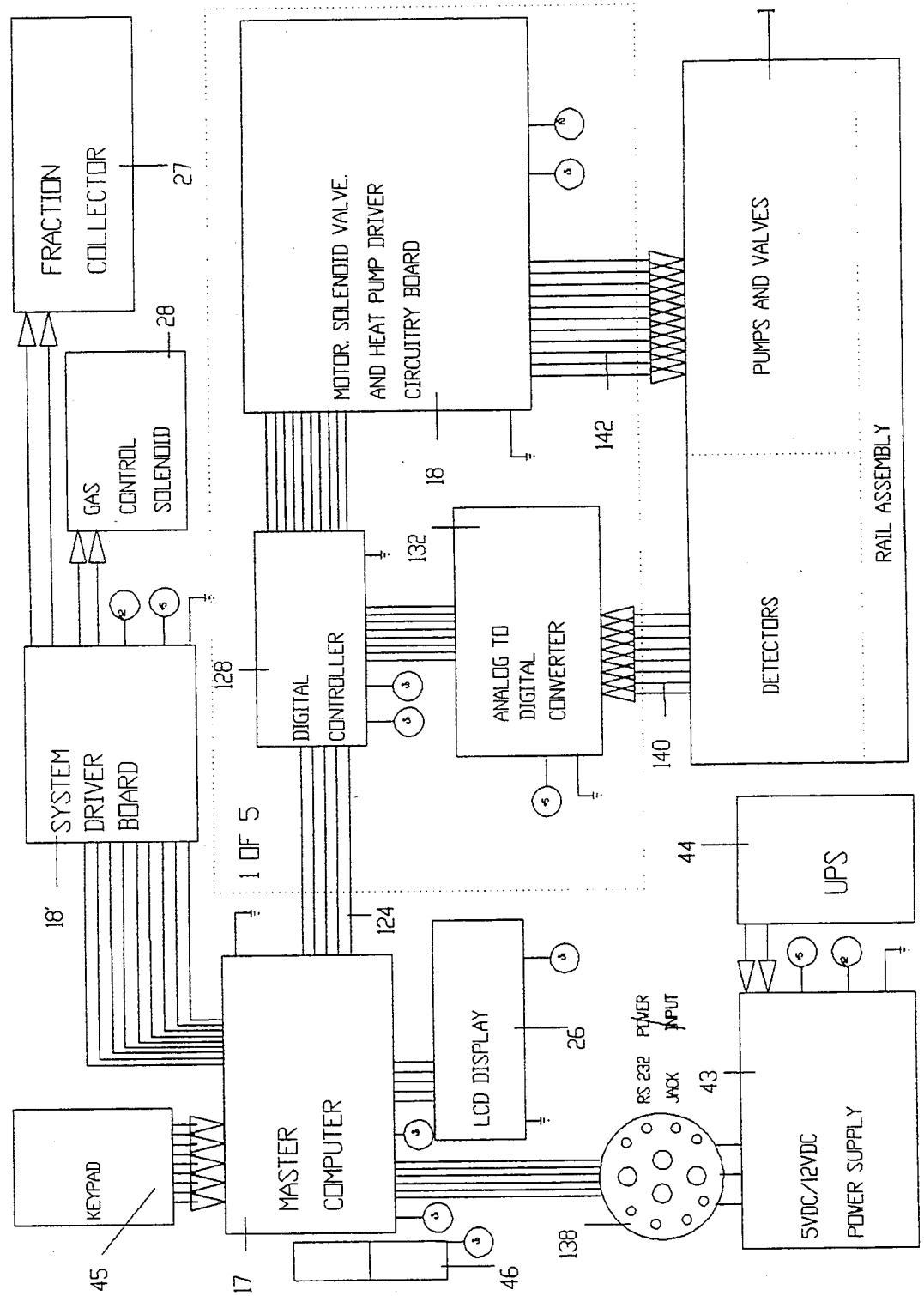
FIG. 16 shows a block schematic diagram of the electronics of the present invention.

With reference, now, to FIG. 16, an explanation of the electronic circuitry of the present invention including the computer control means will now be explained. With reference to FIG. 16, the electronic system includes a power supply 43 which is designed, in a well known manner, to provide 5 volt DC and 12 volt DC power. The power supply 43 may be connected to an external source of power and may be provided with appropriate internal circuitry to convert power received from an external source to 5 volt and 12 volt DC power. Since the various levels of gas supply, media supply and temperature control must be maintained within narrow ranges, to sustain tissue life, a back-up power supply 44 is provided outside the outer containment 47 and is preferably designed to be capable of sustaining operation of the entire device 100 for up to 72 hours should power to the power supply 43 be interrupted. In the preferred embodiment of the present invention, the back-up power supply 44 includes a multiplicity of lithium bromine complex batteries arranged in a plurality of parallel stacks. Preferably, each battery and each stack is properly fused and diode protected. The batteries are also protected by a thermal fuse between each pair of batteries and the entire power supply 48 contains a control panel with a power switch. The power supply 48 also contains various indicators and a sensing means designed to sense interruption of power to the power supply 43 so that activation of the back-up power supply 44 is instantaneous.

The front panel of power supply 48 is provided with pilot, status and warning indicators which give continuous indication of the status of the power supply. An audible alarm exemplified by the enunciator (not shown) is also employed to inform the user that the back-up power supply 44 has been activated.

If desired, the digital circuitry of the inventive electrical circuit can be pre-programmed to telephonically alert someone at a remote location of an extended power interruption or any other critical fault condition sensing in the entire system 100. The keypad 45 may be interfaced to allow manipulation of the software to allow troubleshooting and diagnosis without interruption of main program execution. The display 26 allows visual output of information.

The heart of the electrical circuitry comprises the master computer 17 which may be controlled via the keypad 45 or programmed via RSR32 port 138 and which sends signals through the lines 124 to control the system. The batteries 46 are directly linked to the master computer 17 internally to provide direct back-up power to maintain integrity of any and all soft memories. These soft memories may temporarily store data which is desirable to maintain even when power is interrupted.

The master computer 17 is pre-programmed so that if power is lost to the power supply 43 and the back-up power supply 44 fails or otherwise discharges, the batteries 46 will provide an additional increment of time to protect the master computer 17 until an attendant can arrive to replenish the back-up power supply 44 and/or correct the failure of the power source which is supplying the power supply 43.

In FIG. 16, a single digital controller 128 is illustrated. It should be understood that a plurality of parallel connected digital controllers are provided each directly connected to the master computer 17 via printed circuit mother board 24 (FIG. 6) and each having multiple control functions. Each digital controller 128 is interconnected with various detectors and sensors in the individual rails 1 or in other locations in the device 100 via an analog-to-digital converter 132 which converts the analog signals to digital signals which are readable by the digital controller 128. These detectors include small pH sensors in the liquid pathway, pressure sensors within the inner containment 19, the thermal sensor 15 within the heat sink 13, indicators of proper operation and position of the valves and pumps, and all other sensors. The detectors are schematically represented in FIG. 16 as are the various pumps and valves all of which are shown as located on a particular rail assembly 1.

Also schematically represented in FIG. 16 is the circuitry board 18 which has contained thereon the driver mechanisms for the various pump motors, solenoid valve operators, driver mechanism for the Peltier unit 14, controllers for the ventilation fan 120, and all other system functions. An additional system driver board 18' is also depicted directly connected to the master computer 17 and emitting control signals designed to control the solenoid valve for control of the gas control valve 28 in the gas pathway as illustrated in FIG. 14 and to control the fraction collector device 27 in the fluid pathway as illustrated in FIGS. 8-13.

As should be understood, the electrical circuitry is provided with appropriate test point access for diagnostic and repair purposes as well as integral LED indicators to assist in troubleshooting of electronic problems. The electrical connectors generally designated by the reference numerals 140 and 142 are specifically designed to be water-tight so that they are not affected by any changes in system humidity or any potential possible leaks.

As should be understood from FIG. 16, the electrical circuitry is organized into a network comprised of the master computer 17 which provides for system associated services and which coordinates the activities of the individual slave computers identified as digital controllers 128 in FIG. 16. The master computer 17 also senses power availability and regulates power utilization while providing user interface services by virtue of the keypad 45 and the display 26.

A log of programmed event completion, user interface traffic, and general system conditions is kept by the master computer 17 in an internal memory thereof and may be accessed and displayed as desired. Additionally, although not shown, a printer may be associated with the master computer 17 to permit printing out of data including test results, system condition, information as to power supply continuity, etc. The digital controllers 128 coordinate and control activities on each individual rail 1 and provide equivalent data recording and event logging services which may be transmitted to the master computer 17 for storage and/or display.

Although the description of the electronic circuitry as illustrated in FIG. 16 is quite schematic, when this explanation is taken in conjunction with the specific details of the specific system components as described hereinabove, understanding of the electrical circuitry should be clear. For example, all of the valves have been described in terms of which position the valve head takes when the solenoid is deactivated and which position the valve head takes when the solenoid is activated. Clearly, one skilled in the art with the schematic description of the electrical circuitry as set forth above would understand how to manipulate the keypad 45 to set the valves and pumps for any one of the modes of operation illustrated in FIGS. 9-13, for example. In another example, one skilled in the art would easily understand that the keypad 45 may be manipulated to control activation of the valve 28 in the gas pathway as well as to allow manipulation of the valve 67 and to control the set point of the pressure regulator 20. In the context of the entire system, all of these features take on increasing significance in combination.

With the above description of the preferred embodiment having been made, the specific details of the structure and manner of operation of the present invention should be well understood. With such understanding in mind, numerous applications of the present invention are possible and feasible. Prior to the commencement of any application of the inventive automated cell culture and testing system, the inventive device must be rendered sterile. Several methods of sterilizing the inventive device may be carried out. A first method consists of circulating cold chemical sterilants such as, for example, a sterilant known by the Trade Name "ACTRIL", through the various branches of the flow path of each rail assembly means in accordance with the recommended procedures as provided by the manufacturer. Following this treatment, the inventive device is flushed first with sterile water until no detectable residue is found, followed by minimal essential media for 24 hours. After this treatment regimen has been completed, the system is ready to accept cellular material to be loaded into the bioreactors 8 thereof in a manner which should be understood by those skilled in the art.

Alternatively, each rail assembly means may be irradiated with gamma rays to effect sterilization. This method is highly reliable and effective, however, the gamma rays accelerate aging of elastomeric and plastic components to a high degree. Thus, the use of gamma irradiation to effect sterilization significantly increases costs since many replacement parts must be frequently installed.

Finally, if desired, the individual flow path components may be individually autoclaved and then reassembled under aseptic conditions. It must, again, be stressed, that thorough decontamination of the entire system is essential to assure experimental success.

Once the system has been thoroughly sterilized, it is ready for use. The suggested examples of applications of the inventive device as set forth hereinbelow are merely exemplary, and the potential applications of the inventive device are only limited by the imaginations of its users.

The inventive device 100 is particularly suited to the testing of candidate therapeutics against standardized cells, which may be infectious, malignant or pathologic. In an application where cells carry an infectious agent, aliquots of the material to be tested are presented to a standardized battery of cell types at specific concentrations and for a specific designed duration of time. One bioreactor in each group on a single rail assembly means is not subjected to the treatment and serves as a vehicle/system control. Cellular material is removed from the system via the side port 99 of the bioreactor 8, the material is circulated through a flow cell/light scattering device to measure turbidity, and is thereafter returned to the extracapillary volume of the bioreactor 8. Growth characteristics of the ferments are obtainable from the light scattering results. In addition, cellular material may be sampled at specific points in time to monitor the progress of any experiment. Each bioreactor can thus serve as an internal control. Once removed from the fraction collecting assembly, cells can be subjected to standard histological and biochemical testing to determine effects. An entire experiment can be conducted without breaking sterile barriers due to the self-contained nature of the system 100. An application such as described above enables testing both for antibiotic activity or resistance/susceptibility of an infectious isolate to various standard antibiotics.

In a further intended application for the inventive device 100, activity of natural product extracts or synthetic chemicals may be tested. A standard battery of transformed cell types can be challenged with the material under test, and growth/metabolic characteristics can be measured to determine effects. Standard testing procedures can be used on cells recovered from the system to grade effects. At the same time, normal cells can be included in the battery to determine toxicity to non-transformed tissues. The invention can be modified to allow morphological analysis by including an automated microscope/CCD camera system, bioreactors with integral optical surfaces and a robotic X-Y-Z translator application. In this way, a derivative of the invention can be used to allow direct microscopic observation of living cells during study.

In a further application, any of the currently approved cell-based tissue toxicity, genotoxicity or carcinogenicity testing protocols may be implemented through the use of the inventive device 100 to allow rapid, multiple, and reproducible studies of the toxic, mutational and cancer causing potentials of various liquid, solid or gaseous materials. The various levels of containment and automated test material application/sampling ability makes the present invention especially useful for this particular application. Solid material can be placed in-line to test the effects of leachates on target tissues. Biotransformation of applied materials can be accomplished by connecting, in series with the test bioreactor, a second bioreactor cartridge containing hepatic tissue or S9 extracts of such cells. Aliquots of effluent may be removed to be subjected to analytical testing. In this manner, the chemical nature and exact dose applied to the cells can be determined with a high degree of certainty. Cells may also be observed directly as above. Cells can also be removed from the system periodically to determine activation of oncogenes, etc. Permanent mounts can be produced from cells removed from the system to provide a record of the experiment. The system can be programmed, as desired, so as to not permit deviation from established protocols. In this way, strict compliance with FDA GLP guidelines can be enforced. These aspects permit all experimentation employing the inventive device 100 to be reproducible.

The present invention is especially well suited for automated cell-based experimentation in outer space. The inventive device 100 meets all established NASA electromagnetic radiation, mechanical and safety requirements. The mechanisms of the inventive device are attitude independent, can operate in zero gravity, and the system can operate on the power and voltages available from the Shuttle Orbiter in the mid-deck area thereof. In a configuration specifically adapted for use in the Space Shuttle, the unit is made of a size occupying less than 2 cubic feet.

In a further aspect, the present invention may be easily modified to function as a stand-alone automated cell culture device capable of precisely following programmed protocols. Such use of the present invention will permit isolated biomedical researchers to conduct detailed experiments without the need for technical assistance. At present, the technique of growing living cells and tissues is quite labor intensive, requiring one or more technicians to be present throughout the entire process. Thus, the productivity of an individual experimenter may be increased significantly through the use of the present invention.

In a further aspect, the inventive device may also be used for automated pre-screening of candidate compounds for FDA required premarket acute and chronic toxicity testing. Significant savings in time and finances may be gained by using cultured tissue tests to eliminate toxic and mutagenic compounds from consideration prior to testing in whole animal models. The inventive device can employ a variety of culture vessels with the selection depending upon the nature of the cells and the intended analytical treatment of cultures. In one design, hollow fiber techniques may be employed which allow growth of cells directly on slides/coverslips. The grown cells may be treated at the proper time in situ with inhibitors, drugs, fixatives and stains to allow facile gross morphological analysis, observation of chromosomal morphology and obvious deletions, detection of the presence of micronuclei, disclosure of sister chromatid exchange or other approved methods for analysis of genotoxicity.

In the course of development of the present invention, the following types of tissues have been grown and tested: primary cultures of human bone marrow, human hybridoma cells, primary cultures of rat calvarial bone cells, primary cultures of rat cardiac myocytes, the Yaffe rat L-8 myoblast line, HL-60 human premyelocytic leukemia peripheral blood lymphocyte line, and P388D mouse lymphode neoplasm (which has been used by the National Cancer Institute for cancer chemotherapy screening studies). Additional tissues which are clearly feasible for study in accordance with the teachings of the present invention include primary culture human umbilical vein endothelial cells, human chondrocytes, tendon and synovial cells, whole amphibian embryo, pre-implantation mouse embryo, and co-culture of rat myocytes and neuronal tissue.

Of course, all of the applications set forth above are merely exemplary of the potential applications of the teachings of the present invention. It should now be understood that any experimentation and testing involving any type of living tissue may be carried out through the use of the inventive device 100 and in accordance with the teachings of the present invention.

As such, an invention has been disclosed in terms of a preferred embodiment thereof and applications thereof, which fulfill each and every one of the objects of the invention as set forth hereinabove and provide a new and useful automated cell culture and testing system of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

I claim:
1. A self-contained cell culture and testing system, comprising:
 a) a housing defining a sealed chamber sealed against any incursions;
 b) a plurality of culture systems independently contained within said chamber, each culture system including:
  i) a plurality of bioreactors for containing living cells, each bioreactor including a bioreactor inlet and a bioreactor outlet;
  ii) first supply means for supplying nutrition media or tissue testing media to each of said bioreactor inlets;
  iii) exhaust means for exhausting spent media from each of said bioreactor outlets, said exhaust means including second supply means for supplying said spent media to either a sump or a collection chamber;
  iv) a plurality of fluid pathways, said bioreactor inlet and outlet of each bioreactor being in fluid communication with one of said plurality of fluid pathways such that parallel and non-communicating flow is provided between said first supply means and said exhaust means;
  v) a plurality of recirculation pathways, each bioreactor including one of said plurality of recirculation pathways for recirculating said spent media from said bioreactor outlet back to said bioreactor inlet;
  vi) oxygenation means for oxygenating said spent media in said plurality of recirculation pathways with oxygen containing gas, said oxygenation means comprising a single canister oxygenator including a discrete separate oxygenating path for each recirculation pathway, each said discrete separate oxygenating path including means for introduction of gas to said spent media in a direction countercurrent to a direction of flow of said spent media;
  vii) said exhaust means including first valve means for providing selective flow of said spent media from each bioreactor outlet to said plurality of recirculation pathways or to said second supply means;
  viii) said first supply means including second valve means for providing selective flow of nutrition media or tissue testing media to said plurality of bioreactors;
  ix) said second supply means including third valve means for providing selective flow of said spent media to said sump or to said collection chamber;
  x) thermal control means for controlling temperature of said plurality of bioreactors, said media, and said gas, said thermal control means including a solid metallic heat sink including a heater/cooler mounted directly thereto, said plurality of bioreactors and said oxygenation means being mounted in said heat sink;
 c) a gas pathway including gas supply means for supplying filtered humidified temperature controlled gas to said oxygenation means of each culture system, and gas exhaust means for exhausting spent gasses from said sealed chamber;
 d) computer means including sensing means for sensing heat sink temperature and media pH in each culture system; and control means for controlling position of said first, second and third valve means, and for controlling operation of said thermal control means, said first supply means and said recirculation means of each culture system whereby living cells within said plurality of bioreactors are maintained nourished, oxygenated and within life sustaining temperature limits.

2. The system of claim 1, wherein said sealed chamber is completely contained within a further sealed chamber.

3. The system of claim 1, wherein said first supply means includes a pump.

4. The system of claim 3, wherein said first supply means further includes a container for said nutrition media.

5. The system of claim 4, wherein said first supply means further includes at least one further container for said tissue testing media.

6. The system of claim 5, wherein said container and said at least one further container each comprises a flexible container surrounded by an elastic pressurizing sleeve.

7. The system of claim 5, wherein said second valve means is located upstream of said pump.

8. The system of claim 1, wherein said collection chamber comprises one of a plurality of collection chambers, and further including a manifold downstream of said third valve means and control means associated with said manifold for permitting choosing one of said plurality of collection chambers for receipt of said spent media from said exhaust means.

9. The system of claim 1, wherein said recirculation pathways include a recirculation pump.

10. The system of claim 9, wherein said recirculation pump comprises a single peristaltic-type pump in communication with each recirculation pathway.

11. The system of claim 1, wherein said gas supply means maintains pressure in said sealed chamber above ambient pressure.

12. The system of claim 1, further including a plurality of rail assemblies, each rail assembly supporting one of said plurality of culture systems.

13. The system of claim 1, wherein said heater/cooler comprises a Peltier-type heater/cooler.

14. The system of claim 13, wherein said sensing means includes a temperature sensor embedded in said heat sink of each culture system.

15. The system of claim 1, wherein said computer means includes a main computer and a plurality of controllers connected to said main computer, each of said controllers controlling preassigned system functions under control of said main computer.

16. The system of claim 1, wherein said first, second and third valve means of each culture system are each solenoid operated by said computer means.

* * * * *